US009393296B2

(12) United States Patent
Marques et al.

(10) Patent No.: US 9,393,296 B2
(45) Date of Patent: Jul. 19, 2016

(54) DNA VACCINE AGAINST VIRUS OF YELLOW FEVER

(75) Inventors: Ernesto Torres de Azevedo Marques, Pernambuco (BR); Rafael Dhalia, Pernambuco (BR); Romulo Maciel Filho, Pernambuco (BR)

(73) Assignee: Fundacao Oswaldo Cruz, Rio de Janeiro (BR)

( * ) Notice: Subject to any disclaimer, the term of this patent is extended or adjusted under 35 U.S.C. 154(b) by 514 days.

(21) Appl. No.: 13/504,464

(22) PCT Filed: Oct. 26, 2010

(86) PCT No.: PCT/BR2010/000352
§ 371 (c)(1),
(2), (4) Date: Aug. 14, 2012

(87) PCT Pub. No.: WO2011/050431
PCT Pub. Date: May 5, 2011

(65) Prior Publication Data
US 2012/0308603 A1    Dec. 6, 2012

(30) Foreign Application Priority Data

Oct. 27, 2009    (BR) .................................... 0905645

(51) Int. Cl.
*A61K 39/12*    (2006.01)
*A61K 39/00*    (2006.01)

(52) U.S. Cl.
CPC .............. *A61K 39/12* (2013.01); *A61K 2039/53* (2013.01); *C12N 2770/24134* (2013.01)

(58) Field of Classification Search
None
See application file for complete search history.

(56) References Cited

U.S. PATENT DOCUMENTS 6,171,854 B1 *  1/2001  Galler et al. ................ 435/320.1
6,432,411 B1 *  8/2002  Ivy et al. .................... 424/218.1

FOREIGN PATENT DOCUMENTS

WO    WO 02/080851 A2 *  10/2002

OTHER PUBLICATIONS

Dhalia et al., Anais da Academia Brasileira de Ciencias, 2009, 81(4):663-669.*
Anwar et al., "West Nile premembrane-envelope genetic vaccine encoded as a chimera containing the transmembrane and cytoplasmic domains of a lysosome-associated membrane protein: increased cellular concentration of the transgene product, targeting to the MHC II compartment, and enhanced neutralizing antibody response", Virology, vol. 332, No. 1, pp. 66-77 (2005).
Barrett et al., "The epidemiology of yellow fever in Africa", Microbes and Infection, vol. 4, No. 14, pp. 1459-1468 (2002).
Chen et al., "Identification of two lysosomal membrane glycoproteins", J Cell Biol, vol. 101, No. 1, pp. 85-95 (1985).
De Arruda et al., "DNA vaccine encoding human immunodeficiency virus-1 Gag, targeted to the major histocompatibility complex II compartment by lysosomal-associated membrane protein, elicits enhanced long-term memory response", Immunology, vol. 112, No. 1: 126-133 (2004).
Donnelly et al., "Technical and regulatory hurdles for DNA vaccines", Int J Parasitol, vol. 33, No. 5-6, pp. 457-467 (2003).
Donnelly et al., "DNA vaccines", Life Sci, vol. 60, No. 3, pp. 163-172 (1997).
Drake et al., "Involvement of MIIC-like late endosomes in B cell receptor-mediated antigen processing in murine B cells", J Immunol, vol. 162, No. 2, pp. 1150-1155 (1999).
Guarnieri et al., "The motif Tyr-X-X-hydrophobic residue mediates lysosomal membrane targeting of lysosome-associated membrane protein 1", J Biol Chem, vol. 268, No. 3, pp. 1941-19461 (1993).
Kleijmeer et al., "Major histocompatibility complex class II compartments in human and mouse B lymphoblasts represent conventional endocytic compartments", J Cell Biol, vol. 139, No. 3, pp. 639-649 (1997).
Konishi et al., "Induction of protective immunity against Japanese encephalitis in mice by immunization with a plasmid encoding Japanese encephalitis virus premembrane and envelope genes", J Virol, vol. 72, No. 6, pp. 4925-4930 (1998).
Konishi et al., "A DNA vaccine expressing dengue type 2 virus premembrane and envelope genes induces neutralizing antibody and memory B cells in mice", Vaccine, vol. 18, No. 11-12, pp. 1133-1139 (2000).
Konishi et al., "Comparison of protective efficacies of plasmid DNAs encoding Japanese encephalitis virus proteins that induce neutralizing antibody or cytotoxic T lymphocytes in mice", Vaccine, vol. 21, No. 25-26, pp. 3675-3683 (2003).
Lefeuvre et al., "Current assessment of yellow fever and yellow fever vaccine", Curr Infect Dis Rep, vol. 6, No. 2, pp. 96-104 (2004).
Liu, M. A., "DNA vaccines: a review", J Intern Med, vol. 253, No. 4, pp. 402-410 (2003).
Lu et al., "Dengue 2 PreM-E/LAMP chimera targeted to the MHC class II compartment elicits long-lasting neutralizing antibodies", Vaccine, vol. 21, No. 17-18, pp. 2178-2189 (2003).

(Continued)

*Primary Examiner* — Stacy B Chen
(74) *Attorney, Agent, or Firm* — Caesar Rivise, PC

(57) ABSTRACT

The present invention relates to vaccines of DNA that code for specific viral sequences. The DNA vaccines against yellow fever according to the invention are based on the sequence that codes for the yellow fever virus envelope protein (p/YFE). Besides the wild p/YFE construct, sequence E was also fused with the sequence that codes for the human lysosome-associated membrane protein (h-LAMP), generating the construct (pL/YFE). The results of the invention are considered to be very promising, since both constructs can induce T-cell response against the same epitopes induced by the 17DD vaccine, and the pL/YFE construct can also induce a satisfactory concentration of neutralizing antibodies. The pL/YFE vector was inoculated in mice, before intracerebral challenge with the virus of yellow fever. Surprisingly, 100% of the mice immunized with pL/YFE survived the challenge.

Figure 1:
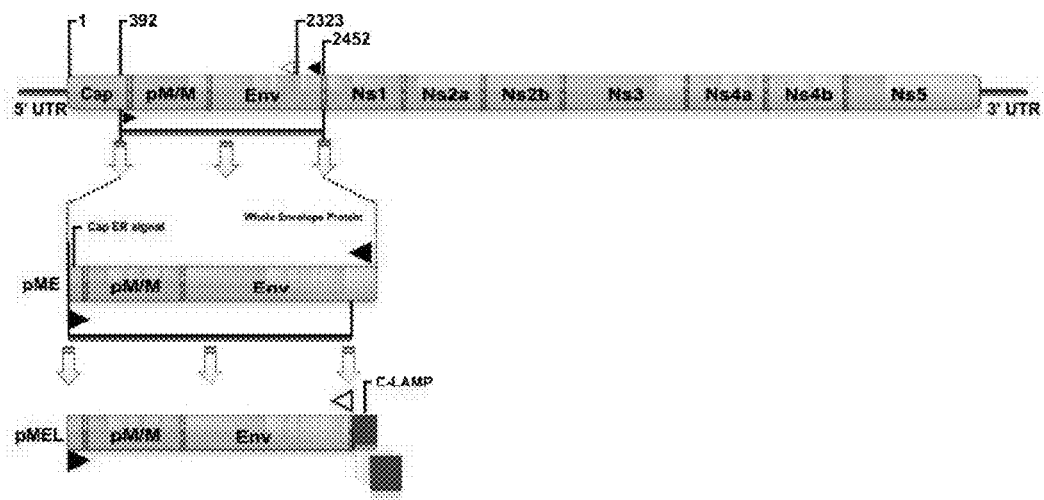

4 Claims, 6 Drawing Sheets
(4 of 6 Drawing Sheet(s) Filed in Color)

(56) References Cited

OTHER PUBLICATIONS

Marques et al., "HIV-1 p55Gag encoded in the lysosome-associated membrane protein-1 as a DNA plasmid vaccine chimera is highly expressed, traffics to the major histocompatibility class II compartment, and elicits enhanced immune responses", J Biol Chem, vol. 278, No. 39, pp. 37926-37936 (2003).

Monath et al., "Single mutation in the flavivirus envelope protein hinge region increases neurovirulence for mice and monkeys but decreases viscerotropism for monkeys: relevance to development and safety testing of live, attenuated vaccines", J Virol, vol. 76, No. 4, pp. 1932-1943 (2002).

Obermueller et al., "The tyrosine motifs of Lamp 1 and LAP determine their direct and indirect targetting to lysosomes", J Cell Sci, vol. 115, Pt 1, pp. 185-194 (2002).

Poland et al., "Persistence of neutralizing antibody 30-35 years after immunization with 17D yellow fever vaccine", Bull World Health Organ, vol. 59, No. 6, pp. 895-900 (1981).

Raviprakash et al., "Immunogenicity of dengue virus type 1 DNA vaccines expressing truncated and full length envelope protein", Vaccine, vol. 18, No. 22, pp. 2426-2434 (2000).

Raviprakash et al., "Synergistic neutralizing antibody response to a dengue virus type 2 DNA vaccine by incorporation of lysosome-associated membrane protein sequences and use of plasmid expressing GM-CSF", Virology, vol. 290, No. 1, pp. 74-82 (2001).

Reinhardt et al., "Development of viremia and humoral and cellular parameters of immune activation after vaccination with yellow fever virus strain 17D: a model of human flavivirus infection", J Med Virol, vol. 56, No. 2, pp. 159-167 (1998).

Robinson et al., "DNA vaccines: basic mechanism and immune responses (Review)", Int J Mol Med, vol. 4, No. 5, pp. 549-555 (1999).

Rohrer et al., "The targeting of Lamp1 to lysosomes is dependent on the spacing of its cytoplasmic tail tyrosine sorting motif relative to the membrane", J Cell Bio, vol. 132, No. 4, pp. 565-576 (1996).

Rowell et al., "Lysosome-associated membrane protein-1-mediated targeting of the HIV-1 envelope protein to an endosomal/lysosomal compartment enhances its presentation to MHC class II-restricted T cells", J Immunol 1995; 155(4): 1818-1828.

Ruff et al., "The enhanced immune response to the HIV gp160/LAMP chimeric gene product targeted to the lysosome membrane protein trafficking pathway", J Biol Chem, vol. 272, No. 13, pp. 8671-8678 (1997).

Abstract of Schultz et al., "Immune modulation in cancer using DNA inoculation—antitumour effect of interleukin-12", Dev Biol (Basel) 2000; 104: 109-114.

Su et al., "Enhanced induction of telomerase-specific CD4(+) T cells using dendritic cells transfected with RNA encoding a chimeric gene product", Cancer Res 2002; 62(17): 5041-5048.

Turley et al., "Transport of peptide-MHC class II complexes in developing dendritic cells", Science 2000; 288(5465): 522-527.

Vasconcelos et al., "Brazilian Yellow Fever Vaccine Evaluation. Serious adverse events associated with yellow fever 17DD vaccine in Brazil: a report of two cases", Lancet 2001; 358(9276): 91-97.

Wu et al., "Development of an effective Japanese encephalitis virus-specific DNA vaccine", Microbes Infect 2006; 8(11): 2578-2586.

Wu et al., "Engineering an intracellular pathway for major histocompatibility complex class II presentation of antigens", Proc Natl Acad Sci USA 1995; 92(25): 11671-11675.

* cited by examiner

```
                            SEQUENCE LISTING

<160> NUMBER OF SEQ ID NOS: 12

<210> SEQ ID NO 1
<211> LENGTH: 42
<212> TYPE: DNA
<213> ORGANISM: Yellow fever virus

<400> SEQUENCE: 1
accgctcgag gccaccatgg gaggattgtc ctcaaggaaa cg                           42

<210> SEQ ID NO 2
<211> LENGTH: 37
<212> TYPE: DNA
<213> ORGANISM: Yellow fever virus

<400> SEQUENCE: 2
accggcggcc gctcagttca agccgccaaa tagcccc                                37

<210> SEQ ID NO 3
<211> LENGTH: 42
<212> TYPE: DNA
<213> ORGANISM: Yellow fever virus

<400> SEQUENCE: 3
accggctagc gccaccatgg gaggattgtc ctcaaggaaa cg                           42

<210> SEQ ID NO 4
<211> LENGTH: 32
<212> TYPE: DNA
<213> ORGANISM: Yellow fever virus

<400> SEQUENCE: 4
accgctcgag gttcaagccg ccaaatagcc cc                                     32

<210> SEQ ID NO 5
<211> LENGTH: 32
<212> TYPE: DNA
<213> ORGANISM: Yellow fever virus

<400> SEQUENCE: 5
accgctcgag acgctgatcc ccatcgctgt gg                                     32

<210> SEQ ID NO 6
<211> LENGTH: 39
<212> TYPE: DNA
<213> ORGANISM: Yellow fever virus
```

<400> SEQUENCE: 6

```
accgtctaga ctagatagtc tggtagcctg cgtgactcc                                39
```

<210> SEQ ID NO 7
<211> LENGTH: 1953
<212> TYPE: DNA
<213> ORGANISM: Yellow fever virus

<400> SEQUENCE: 7

```
ctcgaggcca ccatgggagg attgtcctca aggaaacgcc gttcccatga tgttctgact        60
gtgcaattcc taattttggg aatgctgttg atgacgggtg gagtgacctt ggtgcggaaa       120
aacagatggt tgctcctaaa tgtgacatct gaggacctcg ggaaaacatt ctctgtgggc       180
acaggcaact gcacaacaaa cattttggaa gccaagtact ggtgcccaga ctcaatggaa       240
tacaactgtc ccaatctcag tccgagagag agccagatga cattgattg ctggtgctat        300
ggggtggaaa acgttagagt cgcatatggt aagtgtgact cagcaggcag gtctaggagg       360
tcaagaaggg ccattgactt gcctacgcat gaaaaccatg gtttgaagac ccggcaagaa       420
aaatggatga ctggaagaat gggtgaaagg caactccaaa agattgagag atggttcgtg       480
aggaacccct tttttgcagt gacagctctg accattgcct accttgtggg aagcaacatg       540
acgcaacgag tcgtgattgc cctactggtc ttggctgttg gtccggccta ctcagctcac       600
tgcattggaa ttactgacag ggatttcatt gaggggtgc atggaggaac ttgggttca        660
gctaccctgg agcaagacaa gtgtgtcact gttatggccc ctgacaagcc ttcattggac       720
atctcactag acagtagc cattgataga cctgctgagg cgaggaaagt gtgttacaat        780
gcagttctca ctcatgtgaa gattaatgac aagtgcccca gcactggaga ggcccaccta       840
gctgaagaga cgaaggggga caatgcgtgc aagcgcactt attctgatag aggctggggc       900
aatggctgtg gcctatttgg gaaagggagc attgtggcat gcgccaaatt cacttgtgcc       960
aaatccatga gtttgtttga ggttgatcag accaaaattc agtatgtcat cagagcacaa      1020
ttgcatgtag gggccaagca ggaaaattgg aataccagca ttaagactct caagtttgat      1080
gccctgtcag gctcccagga agtcgagttc attgggtatg gaaaagctac actggaatgc      1140
caggtgcaaa ctgcggtgga cttgtaac agttacatag ctgagatgga aacagagagc       1200
tggatagtgg acagacagtg ggcccaggac ttgaccctgc catggcagag tggaagtggc      1260
ggggtgtgga gagagatgca tcatcttgtc gaattgaac ctccgcatgc cgccactatc        1320
agagtactgg ccctgggaaa ccaggaaggc tccttgaaaa cagctcttac tggcgcaatg      1380
agggttacaa aggacacaaa tgacaacaac ctttacaaac tacatggtgg acatgtttct      1440
tgcagagtga attgtcagc tttgacactc aaggggacat cctacaaaat atgcactgac      1500
aaaatgttt ttgtcaagaa cccaactgac actggccatg gcactgttgt gatgcaggtg       1560
aaagtgccaa aggagccccc tgcaggattc cagtgatag tagctgatga tcttacagcg       1620
gcaatcaata aaggcatttt ggttacagtt aaccccatcg cctcaaccaa tgatgatgaa      1680
gtgctgattg aggtgaaccc acctttttgga gacagctaca ttatcgttgg aagaggagat      1740
tcacgtctca cttaccagtg gcacaaagag ggaagctcaa taggaaagtt gttcactcag      1800
accatgaaag gcgtggaacg cctggccgtc atgggagacg tcgcctggga tttcagctcc      1860
gctgagggt tcttcacttc ggttgggaaa ggaattcata cggtgtttgg ctctgccttt      1920
caggggctat ttggcggctt gaactgatct aga                                  1953
```

<210> SEQ ID NO 8
<211> LENGTH: 2067
<212> TYPE: DNA
<213> ORGANISM: Yellow fever virus

<400> SEQUENCE: 8

```
gctagcgcca ccatgggagg attgtcctca aggaaacgcc gttcccatga tgttctgact      60
gtgcaattcc taattttggg aatgctgttg atgacgggtg gagtgacctt ggtgcggaaa     120
aacagatggt tgctcctaaa tgtgacatct gaggacctcg ggaaaacatt ctctgtgggc     180
acaggcaact gcacaacaaa cattttggaa gccaagtact ggtgcccaga ctcaatggaa     240
tacaactgtc ccaatctcag tccgagagag gagccagatg acattgattg ctggtgctat     300
ggggtggaaa acgttagagt cgcatatggt aagtgtgact cagcaggcag gtctaggagg     360
tcaagaaggg ccattgactt gcctacgcat gaaaaccatg gtttgaagac ccggcaagaa     420
aaatggatga ctggaagaat gggtgaaagg caactccaaa agattgagag atggttcgtg     480
aggaacccct tttttgcagt gacagctctg accattgcct accttgtggg aagcaacatg     540
acgcaacgag tcgtgattgc cctactggtc ttggctgttg gtccggccta ctcagctcac     600
tgcattggaa ttactgacag ggatttcatt gagggggtgc atggaggaac ttgggttca      660
gctaccctgg agcaagacaa gtgtgtcact gttatggccc ctgacaagcc ttcattggac     720
atctcactag agacagtagc cattgataga cctgctgagg cgaggaaagt gtgttacaat     780
gcagttctca ctcatgtgaa gattaatgac aagtgcccca gcactggaga ggcccaccta     840
gctgaagaga cgaagggga caatgcgtgc aagcgcactt attctgatag aggctggggc     900
aatggctgtg gcctatttgg aaagggagc attgtggcat gcgccaaatt cacttgtgcc     960
aaatccatga gtttgtttga ggttgatcag accaaaattc agtatgtcat cagagcacaa    1020
ttgcatgtag ggccaagca ggaaaattgg aataccagca ttaagactct caagtttgat    1080
gccctgtcag gctcccagga agtcgagttc attgggtatg gaaaagctac actggaatgc    1140
caggtgcaaa ctgcggtgga ctttggtaac agttacatag ctgagatgga aacagagagc    1200
tggatagtgg acagacagtg ggcccaggac ttgaccctgc catggcagag tggaagtggc    1260
ggggtgtgga gagagatgca tcatcttgtc gaatttgaac ctccgcatgc cgccactatc    1320
agagtactgg ccctgggaaa ccaggaaggc tccttgaaaa cagctcttac tggcgcaatg    1380
agggttacaa aggacacaaa tgacaacaac ctttacaaac tacatggtgg acatgtttct    1440
tgcagagtga aattgtcagc tttgacactc aaggggacat cctacaaaat atgcactgac    1500
aaaatgtttt ttgtcaagaa cccaactgac actggccatg gcactgttgt gatgcaggtg    1560
aaagtgccaa aggagcccc ctgcaggatt ccagtgatag tagctgatga tcttacagcg    1620
gcaatcaata aaggcatttt ggttacagtt aaccccatcg cctcaaccaa tgatgatgaa    1680
gtgctgattg aggtgaaccc accttttgga gacagctaca ttatcgttgg aagaggagat    1740
tcacgtctca cttaccagtg gcacaaagag ggaagctcaa taggaaagtt gttcactcag    1800
accatgaaag cgtggaacg cctggccgtc atgggagacg tcgcctggga tttcagctcc    1860
gctggagggt tcttcacttc ggttgggaaa ggaattcata cggtgtttgg ctctgccttt    1920
caggggctat ttggcggctt gaacctcgag acgctgatcc ccatcgctgt gggtggtgcc    1980
ctggcggggc tggtcctcat cgtcctcatc gcctacctcg tcggcaggaa gaggagtcac    2040
gcaggctacc agactatcta gtctaga                                         2067
```

<210> SEQ ID NO 9
<211> LENGTH: 2079
<212> TYPE: DNA
<213> ORGANISM: Yellow fever virus

<400> SEQUENCE: 9

```
gtcgacgcta gcaccatgga actcgagggc ggcctgagca gccggaagcg gcggagccac        60
gacgtgctga ccgtgcagtt cctgatcctg ggcatgctgc tgatgacagg cggcgtgacc       120
ctggtgcgga agaaccggtg gctgctgctg aacgtgacca gcgaggacct gggcaagacc       180
ttcagcgtgg gcaccggcaa ctgcaccacc aacatcctgg aagccaagta ctggtgcccc       240
gacagcatga atacaactg ccccaacctg agccccagag aggaacccga cgacatcgac       300
tgctggtgct acggcgtgga aacgtgcgg gtggcctacg gcaagtgcga cagcgccggc       360
agaagccggc ggtccagacg cgctattgat ctccccaccc acgagaacca cggcctgaaa       420
acccggcagg aaaagtggat gaccggccgg atgggcgagc ggcagctgca gaagatcgag       480
cgctggttcg tgcggaaccc cttcttcgcc gtgaccgccc tgacaatcgc ctacctggtg       540
ggcagcaaca tgacccagcg ggtggtgatc gccctgctgg tgctggccgt gggccctgcc       600
tacagcgccc actgcatcgg catcaccgac cgggacttca tcgagggcgt gcacggcggc       660
acatgggtgt ccgccaccct ggaacaggac aagtgcgtga ccgtgatggc ccccgacaag       720
cccagcctgg acatcagcct ggaaaccgtg gccatcgaca cccgccga ggcccggaaa       780
gtgtgctaca cgccgtgct gacccacgtg aagatcaacg ataaatgtcc ctccacagga       840
gaagctcacc tggccgagga aaacgagggc gacaacgcct gcaagcggac ctacagcgac       900
cggggctggg gcaatggctg cggcctgttc ggcaagggca catcgtggc ctgcgccaag       960
ttcacctgtg ccaagagcat gagcctgttc gaggtggacc agaccaagat ccagtacgtg      1020
atccgggccc agctgcacgt gggcgccaag caggaaaact ggaacaccag catcaagacc      1080
ctgaagttcg acgccctgag cggcagccag gaagtggagt catcggcta cggcaaggcc      1140
acactggaat gccaggtgca gaccgccgtg gacttcggca acagctatat cgccgagatg      1200
gaaaccgaga gctggatcgt ggaccggcag tgggcccagg acctgaccct gccctggcag      1260
agcggcagcg gcggagtgtg gcgggagatg caccacctgg tggagttcga gccccccac      1320
gccgccacca tccgggtgct ggccctgggg aaccaggaag ctccctgaa acagctctc      1380
acagggcta tgcgggtgac caaggacacc aacgacaaca acctgtacaa gctgcacggc      1440
gggcacgtga gctgccgggt gaagctgtcc gccctgaccc tgaagggcac cagctacaag      1500
atctgcaccg acaagatgtt cttcgtgaag aaccccaccg cacccggcca cggcaccgtg      1560
gtgatgcagg tgaaggtgcc caaggcgcc ccttgccgga tccccgtgat cgtggccgac      1620
gacctgacag ccgccatcaa caagggcatc ctggtgaccg tgaaccctat cgccagcacc      1680
aacgacgacg aggtgctgat cgaggtgaac ccccccttcg gcgactccta catcatcgtg      1740
ggcaggggcg acagccggct gacctaccag tggcacaaag agggcagcag catcggcaag      1800
ctgttcaccc agacaatgaa gggcgtggag cggctggccg tgatggggga cgtggcctgg      1860
gacttcagct ctgccggcgg attcttcacc tccgtgggca agggcattca caccgtgttc      1920
ggcagcgcct tccagggcct gtttggcgg ctgaacgaat tcacgctgat ccccatcgct      1980
gtgggtggtg ccctgcgg gctggtcctc atcgtcctca tcgcctacct cgtcggcagg      2040
aagaggagtc acgcaggcta ccagactatc tagggtacc                             2079
```

<210> SEQ ID NO 10
<211> LENGTH: 3208
<212> TYPE: DNA
<213> ORGANISM: Yellow fever virus

<400> SEQUENCE: 10

| | | | | | | |
|---|---|---|---|---|---|---|
| gtcgactagc | atggcgcccc | gcagcgcccg | gcgacccctg | ctgctgctac | tgctgttgct | 60 |
| gctgctcggc | tcatgcatt | gtgcgtcagc | agcaatgttt | atggtgaaaa | atggcaacgg | 120 |
| gaccgcgtgc | ataatggcca | acttctctgc | tgccttctca | gtgaactacg | acaccaagag | 180 |
| tggccctaag | aacatgaccc | ttgacctgcc | atcagatgcc | acagtggtgc | tcaaccgcag | 240 |
| ctcctgtgga | aaagagaaca | cttctgaccc | cagtctcgtg | attgcttttg | gaagaggaca | 300 |
| tacactcact | ctcaatttca | cgagaaatgc | aacacgttac | agcgttcagc | tcatgagttt | 360 |
| tgtttataac | ttgtcagaca | cacccttttt | ccccaatgcg | agctccaaag | aaatcaagac | 420 |
| tgtggaatct | ataactgaca | tcagggcaga | tatagataaa | aaatacagat | gtgttagtgg | 480 |
| cacccaggtc | cacatgaaca | acgtgaccgt | aacgctccat | gatgccacca | tccaggcgta | 540 |
| ccttttccaac | agcagcttca | gcaggggaga | gacacgctgt | gaacaagaca | ggccttcccc | 600 |
| aaccacagcg | cccctgcgc | cacccagccc | ctcgccctca | cccgtgccca | agagcccctc | 660 |
| tgtggacaag | tacaacgtga | gcggcaccaa | cgggacctgc | ctgctggcca | gcatgggct | 720 |
| gcagctgaac | ctcacctatg | agaggaagga | caacacgacg | gtgacaaggc | ttctcaacat | 780 |
| caaccccaac | aagacctcgg | ccagcgggag | ctgcggcgcc | cacctggtga | ctctggagct | 840 |
| gcacagcgag | ggcaccaccg | tcctgctctt | ccagttcggg | atgaatgcaa | gttctagccg | 900 |
| gtttttccta | caaggaatcc | agttgaatac | aattcttcct | gacgccagag | accctgcctt | 960 |
| taaagctgcc | aacggctccc | tgcgagcgct | gcaggccaca | gtcggcaatt | cctacaagtg | 1020 |
| caacgcggag | gagcacgtcc | gtgtcacgaa | ggcgttttca | gtcaatatat | tcaaagtgtg | 1080 |
| ggtccaggct | ttcaaggtgg | aaggtggcca | gtttggctct | gtggaggagt | gtctgctgga | 1140 |
| cgagaacagc | ctcgagggcg | gcctgagcag | ccggaagcgg | cggagccacg | acgtgctgac | 1200 |
| cgtgcagttc | ctgatcctgg | gcatgctgct | gatgacaggc | ggcgtgaccc | tggtgcggaa | 1260 |
| gaaccggtgg | ctgctgctga | acgtgaccag | cgaggacctg | gcaagacct | tcagcgtggg | 1320 |
| caccggcaac | tgcaccacca | acatcctgga | agccaagtac | tggtgccccg | acagcatgga | 1380 |
| atacaactgc | cccaacctga | gcccagaga | ggaacccgac | gacatcgact | gctggtgcta | 1440 |
| cggcgtggag | aacgtgcggg | tggcctacgg | caagtgcgac | agcgccggca | gaagccggcg | 1500 |
| gtccagacgc | gctattgatc | tccccaccca | cgagaaccac | ggcctgaaaa | cccggcagga | 1560 |
| aaagtggatg | accggccgga | tgggcgagcg | gcagctgcag | aagatcgagc | gctggttcgt | 1620 |
| gcggaaccc | ttcttcgccg | tgaccgccct | gacaatcgcc | tacctggtgg | gcagcaacat | 1680 |
| gacccagcgg | gtggtgatcg | ccctgctggt | gctggccgtg | ggccctgcct | acagcgccca | 1740 |
| ctgcatcggc | atcaccgacc | gggacttcat | cgagggcgtg | cacggcggca | catgggtgtc | 1800 |
| cgccaccctg | gaacaggaca | agtgcgtgac | cgtgatggcc | cccgacaagc | ccagcctgga | 1860 |
| catcagcctg | gaaccgtgg | ccatcgacag | accgccgag | gccggaaag | tgtgctacaa | 1920 |
| cgccgtgctg | acccacgtga | agatcaacga | taaatgtccc | tccacaggag | aagctcacct | 1980 |
| ggccgaggaa | aacgagggcg | acaacgcctg | caagcggacc | tacagcgacc | ggggctgggg | 2040 |
| caatggctgc | ggcctgttcg | gcaagggcag | catcgtggcc | tgcgccaagt | tcacctgtgc | 2100 |
| caagagcatg | agcctgttcg | aggtggacca | gaccaagatc | cagtacgtga | tccgggccca | 2160 |

```
gctgcacgtg ggcgccaagc aggaaaactg gaacaccagc atcaagaccc tgaagttcga    2220
cgccctgagc ggcagccagg aagtggagtt catcggctac ggcaaggcca cactggaatg    2280
ccaggtgcag accgccgtgg acttcggcaa cagctatatc gccgagatgg aaaccgagag    2340
ctggatcgtg gaccggcagt gggcccagga cctgaccctg ccctggcaga gcggcagcgg    2400
cggagtgtgg cgggagatgc accacctggt ggagttcgag ccccccacg ccgccaccat     2460 ccgggtgctg gccctgggga accaggaagg ctccctgaaa acagctctca caggggctat    2520
gcgggtgacc aaggacacca acgacaacaa cctgtacaag ctgcacggcg gcacgtgag    2580 ctgccgggtg aagctgtccg ccctgaccct gaagggcacc agctacaaga tctgcaccga    2640
caagatgttc ttcgtgaaga accccaccga caccggccac ggcaccgtgg tgatgcaggt    2700
gaaggtgccc aaaggcgccc cttgccggat ccccgtgatc gtggccgacg acctgacagc    2760
cgccatcaac aagggcatcc tggtgaccgt gaaccctatc gccagcacca acgacgacga    2820
ggtgctgatc gaggtgaacc cccccttcgg cgactcctac atcatcgtgg gcaggggcga    2880
cagccggctg acctaccagt ggcacaaaga gggcagcagc atcggcaagc tgttcacccc    2940
gacaatgaag ggcgtggagc ggctggccgt gatgggggac gtggcctggg acttcagctc    3000
tgccggcgga ttcttcacct ccgtgggcaa gggcattcac accgtgttcg gcagcgcctt    3060
ccagggcctg tttggcggcc tgaacgaatt cacgctgatc cccatcgctg tgggtggtgc    3120
cctggcgggg ctggtcctca tcgtcctcat cgcctacctc gtcggcagga agaggagtca    3180
cgcaggctac cagactatct agggtacc                                      3208

<210> SEQ ID NO 11
<211> LENGTH: 2079
<212> TYPE: DNA
<213> ORGANISM: Yellow fever virus

<400> SEQUENCE: 11
gtcgacgcta gcaccatgga actcgaggga gggctgagca gcagaaaacg acggagccat      60
gatgtgctga ctgtgcagtt tctgatcctt gggatgctgc tgatgacggg aggcgtgaca     120
cttgtgagga agaataggtg gctgctgctc aatgtgactt ccgaggacct ggggaaaacc     180
tttagcgtgg gaacgggtaa ctgtaccaca acatactcg aagctaagta ctggtgccca      240
gattcaatgg agtacaattg tccaaaacctg agcccgaggg aagaacctga tgacatagac    300
tgctggtgct acggagtcga aaacgtcaga gtggcttacg gtaagtgcga cagcgcagga    360
cgcagccgtc ggagtaggag agctatagac ctgccgacac acgagaacca cggcttgaaa    420
acacggcagg agaagtggat gacaggcagg atgggagaga gacaactgca aaagatcgag    480
cggtggttcg ttcggaatcc cttcttcgca gttacggcgc tgactatagc ctatttggtg    540
ggctccaaca tgactcagag agtggtgata gcccttctgg ttctggccgt ggggcccgcc    600
tatagcgccc actgcatcgg gattaccgac agggatttca ttgaaggcgt gcacggaggc    660
acctgggtgt ctgccacact cgaacaggat aagtgcgtga cagttatggc acccgacaaa    720
cctagccttg atatcagttt ggaaaccgtc gcgatagacc gtcctgccga ggccaggaaa    780
gtgtgctaca cgctgtgct gacgcacgtg aagatcaacg ataagtgtcc ctctacaggc    840
gaagcgcacc tggcagagga gaacgagggg gacaacgcct gcaagcgcac ttacagcgac    900
aggggttggg gaaacggctg tggcctgttt ggcaaaggtt ccatcgttgc ttgtgctaag    960
ttcacctgtg ccaaatccat gtcactttc gaggtggatc agactaagat tcaatacgtg    1020
attcgagcac agctgcacgt gggagcgaaa caagagaact ggaataccct aatcaagact    1080
```

| | |
|---|---|
| ctgaagttcg acgcactgag tggtagccag gaagtcgagt ttatcggcta cgggaaagca | 1140 |
| accctggagt gtcaggtgca gacagcagtg gactttggga atagctacat agcagagatg | 1200 |
| gaaacagaat cctggatcgt ggaccgtcag tgggctcagg atctgaccct ccttggcaa | 1260 |
| agtggatcag gcggtgtgtg gagagagatg catcacttgg ttgaatttga gccaccgcac | 1320 |
| gctgctacca ttcgggtcct ggccttgggc aatcaggagg gcagtctgaa aactgccctg | 1380 |
| accggagcca tgcgggtgac aaaagatacg aacgacaaca acctctacaa actgcacggc | 1440 |
| ggacacgtca gctgcagagt gaaactgtca gcactgacct tgaaggggac tagctacaag | 1500 |
| atttgcacag ataagatgtt cttcgtgaag aatcccactg atactgggca cggcactgtg | 1560 |
| gtgatgcaag tgaaggtccc aaagggagcc ccttgtcgaa tccctgtgat tgtggctgac | 1620 |
| gatctgaccg ctgctatcaa caaaggaatc ctggttaccg tgaatcccat cgcgagtaca | 1680 |
| aacgacgacg aagtcctgat cgaggtgaat ccacccttg gcgacagcta catcattgtc | 1740 |
| gggaggggag acagcaggct gacgtatcag tggcacaaag aagggtcctc aatcgggaag | 1800 |
| ctgtttaccc agacaatgaa aggcgtggag cgactggccg tgatgggaga cgtggcctgg | 1860 |
| gacttctcca gtgccggcgg cttctttacc tccgtgggca agggaatcca taccgtgttt | 1920 |
| ggctcagcct ttcagggact gtttggtggt ttgaacgaat tcacgctgat ccccatcgct | 1980 |
| gtgggtggtg ccctggcggg gctggtcctc atcgtcctca tcgcctacct cgtcggcagg | 2040 |
| aagaggagtc acgcaggcta ccagactatc tagggtacc | 2079 |

<210> SEQ ID NO 12
<211> LENGTH: 3208
<212> TYPE: DNA
<213> ORGANISM: Yellow fever virus

<400> SEQUENCE: 12

| | |
|---|---|
| gtcgactagc atggcgcccc gcagcgcccg gcgacccctg ctgctgctac tgctgttgct | 60 |
| gctgctcggc tcatgcatt gtgcgtcagc agcaatgttt atggtgaaaa atggcaacgg | 120 |
| gaccgcgtgc ataatggcca acttctctgc tgccttctca gtgaactacg acaccaagag | 180 |
| tggccctaag aacatgaccc ttgacctgcc atcagatgcc acagtggtgc tcaaccgcag | 240 |
| ctcctgtgga aaagagaaca cttctgaccc cagtctcgtg attgcttttg aagaggaca | 300 |
| tacactcact ctcaatttca gagaaatgc aacacgttac agcgttcagc tcatgagttt | 360 |
| tgtttataac ttgtcagaca cacacccttt ccccaatgcg agctccaaag aaatcaagac | 420 |
| tgtggaatct ataactgaca tcagggcaga tatagataaa aaatacagat gtgttagtgg | 480 |
| cacccaggtc cacatgaaca acgtgaccgt aacgctccat gatgccacca tccaggcgta | 540 |
| cctttccaac agcagcttca gcaggggaga gacacgctgt gaacaagaca ggccttcccc | 600 |
| aaccacagcg cccctgcgc cacccagccc ctcgccctca cccgtgccca gagcccctc | 660 |
| tgtggacaag tacaacgtga gcggcaccaa cggacctgc ctgctggcca gcatggggct | 720 |
| gcagctgaac ctcacctatg agaggaagga caacacgacg gtgacaaggc ttctcaacat | 780 |
| caaccccaac aagacctcgg ccagcgggag ctgcggcgcc cacctggtga ctctggagct | 840 |
| gcacagcgag ggcaccaccg tcctgctctt ccagttcggg atgaatgcaa gttctagccg | 900 |
| gttttttccta caaggaatcc agttgaatac aattcttcct gacgccagag accctgcctt | 960 |
| taaagctgcc aacggctccc tgcgagcgct gcaggccaca gtcggcaatt cctacaagtg | 1020 |
| caacgcggag gagcacgtcc gtgtcacgaa ggcgttttca gtcaatatat tcaaagtgtg | 1080 |
| ggtccaggct ttcaaggtgg aaggtggcca gtttggctct gtggaggagt gtctgctgga | 1140 |

-continued

```
cgagaacagc ctcgagggag ggctgagcag cagaaaacga cggagccatg atgtgctgac    1200
tgtgcagttt ctgatccttg ggatgctgct gatgacggga ggcgtgacac ttgtgaggaa    1260
gaataggtgg ctgctgctca atgtgacttc cgaggacctg gggaaaacct ttagcgtggg    1320
aacgggtaac tgtaccacaa acatactcga agctaagtac tggtgcccag attcaatgga    1380
gtacaattgt ccaaacctga gcccgaggga agaacctgat gacatagact gctggtgcta    1440
cggagtcgaa aacgtcagag tggcttacgg taagtgcgac agcgcaggac gcagccgtcg    1500
gagtaggaga gctatagacc tgccgacaca cgagaaccac ggcttgaaaa cacggcagga    1560
gaagtggatg acaggcagga tgggagagag acaactgcaa aagatcgagc ggtggttcgt    1620
tcggaatccc ttcttcgcag ttacggcgct gactatagcc tatttggtgg gctccaacat    1680
gactcagaga gtggtgatag cccttctggt tctggccgtg gggcccgcct atagcgccca    1740
ctgcatcggg attaccgaca gggatttcat tgaaggcgtg cacggaggca cctgggtgtc    1800
tgccacactc gaacaggata agtgcgtgac agttatggca cccgacaaac ctagccttga    1860
tatcagtttg gaaaccgtcg cgatagaccg tcctgccgag gccaggaaag tgtgctacaa    1920
cgctgtgctg acgcacgtga agatcaacga taagtgtccc tctacaggcg aagcgcacct    1980
ggcagaggag aacgaggggg acaacgcctg caagcgcact tacagcgaca ggggttgggg    2040
aaacggctgt ggcctgtttg gcaaaggttc catcgttgct tgtgctaagt tcacctgtgc    2100
caaatccatg tcacttttcg aggtggatca gactaagatt caatacgtga ttcgagcaca    2160
gctgcacgtg ggagcgaaac aagagaactg gaatacctca atcaagactc tgaagttcga    2220
cgcactgagt ggtagccagg aagtcgagtt tatcggctac gggaaagcaa ccctggagtg    2280
tcaggtgcag acagcagtgg actttgggaa tagctacata gcagagatgg aaacagaatc    2340
ctggatcgtg gaccgtcagt gggctcagga tctgacccct ccttggcaaa gtggatcagg    2400
cggtgtgtgg agagagatgc atcacttggt tgaatttgag ccaccgcacg ctgctaccat    2460
tcgggtcctg gccttgggca atcaggaggg cagtctgaaa actgccctga ccggagccat    2520
gcgggtgaca aaagatacga acgacaacaa cctctacaaa ctgcacggcg gacacgtcag    2580
ctgcagagtg aaactgtcag cactgacctt gaaggggact agctacaaga tttgcacaga    2640
taagatgttc ttcgtgaaga atcccactga tactgggcac ggcactgtgg tgatgcaagt    2700
gaaggtccca aagggagccc cttgtcgaat ccctgtgatt gtggctgacg atctgaccgc    2760
tgctatcaac aaaggaatcc tggttaccgt gaatcccatc gcgagtacaa acgacgacga    2820
agtcctgatc gaggtgaatc caccctttgg cgacagctac atcattgtcg ggaggggaga    2880
cagcaggctg acgtatcagt ggcacaaaga agggtcctca atcgggaagc tgtttaccca    2940
gacaatgaaa ggcgtggagc gactggccgt gatgggagac gtggcctggg acttctccag    3000
tgccggcggc ttctttacct ccgtgggcaa gggaatccat accgtgtttg gctcagcctt    3060
tcagggactg tttggtggtt tgaacgaatt cacgctgatc cccatcgctg tgggtggtgc    3120
cctggcgggg ctggtcctca tcgtcctcat cgcctacctc gtcggcagga agaggagtca    3180
cgcaggctac cagactatct agggtacc                                       3208
```

DNA VACCINE AGAINST VIRUS OF YELLOW FEVER

FIELD OF THE INVENTION

The present invention is directed to a DNA vaccine optimized based on the region encoding the envelope of the Yellow Fever virus fused to an Association Protein to the Lysosomal Membrane—LAMP, able to process the encoded antigen and present it to the immune system through MHC II route.

BACKGROUND OF INVENTION

The virus of Yellow Fever (YF) is considered the prototype of the Flaviviridae family, also represented by several other medically important viruses that cause serious diseases such as Dengue, Japanese Encephalitis and West Nile Fever (Barrett, 2002). According to World Health Organization (WHO) more than 200,000 cases of YF infection, including 30,000 deaths occur annually worldwide (90% of disseminated cases in Africa). The safest strategy for disease prevention remains vaccination, whereas there is still no effective drug against infection by YF. Over the past 70 years more than 400 million people globally were vaccinated with YF-attenuated virus (17DD), considered very safe and effective. Despite the success of mass vaccination with 17DD, which is capable of inducing both lasting response of neutralizing antibody as cytotoxic T cell response (Poland, Calisher et al., 1981; Reinhardt, Jaspert et al., 1998), adverse severe events (as a result of vaccination) has been systematically reported in the literature [reviewed in (Liu, 2003)]. In some cases, immunization has been directly associated with increased severity of symptoms (Monath, Arroyo et al., 2002) and may even lead to fatal reactions (Vasconcelos, Luna et al., 2001; Lefeuvre, Marianneau et al., 2004). In this scenario the development of new vaccination strategy, such as DNA vaccines encoding specific viral sequences (Donnelly, Ulmer et al., 1997; Lewis and Babiuk, 1999; Robinson, 1999; Schultz, Pavlovic et al., 2000) is of fundamental importance for the development of even safer vaccine strategies.

The genome of Yellow Fever Virus (YFV) is arranged in a positive mRNA molecule, approximately 10.8 Kb flanked by the structures of 5 'cap and 3rd handle' terminal not poly adenilada. The RNA YFV encodes three structural genes (Capsid—C, Membrane—M and Envelope—E) and 7 genes that encode non-structural proteins (NS1, NS2a, NS2b, NS3, NS4a, NS4b and NS5). During assembly of virus the carboxy-terminal domain of protein C acts as a signal sequence for translocation of the precursor PreM/M into the lumen of the endoplasmic reticulum (ER) of the host cell, allowing proper maturation of the M and E protein. Co-expression of proteins PreM/M and flavivirus, in mammalian cells results in the formation of pseudo-viral particles capable of inducing humoral response (Raviprakash, Kochel et al., 2000; Wu, Li et al. 2006), because the protein E is the major target for neutralizing antibodies.

Co-expression of proteins PreM/M and E, as vaccine strategy, has been described as being capable of inducing the neutralizing antibodies productions against the virus of Japanese Encephalitis and Dengue (Konishi, Yamaoka et al., 1998; Konishi, Yamaoka et al., 2000; Konishi, Ajiro. et al, 2003). However, these vaccines failed to induce long-term response with appropriate titers of neutralizing antibodies (Lu, et al Raviprakash, 2003). The inefficiency of these formulations is probably related to the mechanism of presentation of these antigens to the immune system of hosts. Most of endogenously produced antigens, characteristic of DNA vaccines, are kidnapped and presented to the host immune system by MHC I molecules. For a satisfactory immune response, with high neutralizing antibodies production, it is critical that the antigens are presented to cells of the T helper $CD4^+$ type by MHC II molecules. The processing and the antigen presentation by MHC II induces the activation of T $CD4^+$ cells that is vital to the functioning of genetic vaccines, as has already been demonstrated in studies of deletion of MHC II (Raviprakash, Marques et al., 2001) and $CD4^+$ depletion in mice (Lu et al Raviprakash, 2003). The activation of $CD4^+$ cells is essential for the induction of $CD8^+$ response, development of memory cells (Marques, Chikhlikar et al., 2003) and clonal expansion of antigen-specific B cell (De Arruda, Chikhlikar et al., 2004). So that antigens endogenously produced are directed to molecules of class II, instead class I, it is necessary that these proteins are fused to peptides signs which direct them for the lysosomal compartment of the cell.

The possibility of directing endogenously produced antigens, for processing via MHC II was strongly increased after the discovery of a type I transmembrane protein, called Lysosome-Associated Membrane Protein—LAMP (Chen, Murphy et al. 1985). LAMP is a protein that binds to the outer membrane of the lysosome via its carboxy-terminal sequence YXXØ, present in a cytoplasmic tail of 11 amino acids (Guarnieri, Arterburn et al., 1993; Rohrer, Schweizer et al., 1996; Obermüller, Kiecke et al., 2002). The LAMP intracellular traffic includes specialized multilaminar compartments of immature Antigen-Presenting Cells (APC), called MIIC and CIIV, where processing and formation of antigenic peptide-MHC II complex takes place (Kleijmeer, Morkowski et al. 1997; Drake, Lewis et al., 1999; Turley, Inaba et al., 2000). The finding of colocalization of LAMP and MHC II molecules allows its use as support for chimeric antigen, containing the sequences of LAMP targets, aimed at direction antigen processing for MHC II compartment. Many works have demonstrated that antigens fused to the LAMP (antigen/LAMP) are capable of generating a higher proliferative activity of specific antigen lymphocytes, high titers of antibodies and intense cytotoxic T activity in relation to the wild non-fused antigens to the LAMP (Rowell, Ruff et al., 1995; Wu, Guarneri et al., 1995; Ruff, Guarneri et al., 1997; Raviprakash, Marques et al., 2001; Su, Vieweg et al., 2002; Donnelly, Berry et al., 2003; Anwar, Chandrasekaran et al., 2005).

The attenuated virus vaccine 17DD has been produced on the campus of Manguinhos—FIOCRUZ/RJ since 1937, i.e. at least 70 years. The mass immunization with the vaccine 17DD, as well as the systematic fight against the transmission vector of Yellow Fever (*Aedes aegypti*), were and remains crucial strategies for disease control in the country. Despite the efficacy and safety of the vaccine 17DD, it is not recommended for infants, pregnant women, and people who have immunodeficiencies and who are allergic to egg proteins (substrate for vaccine 17DD production). It is estimated that approximately 5% of the population presents allergies and/or side effects in response to the vaccine, possibly culminating in rare cases of death caused by vaccination.

Recently, facing the death of monkeys in wildlife regions where YFV circulates, the population began to panic at the speculations of the re-introduction of urban Yellow Fever in the country. Considering the risk of infection prevalent in tropical areas, the invasion of the urban environment by the vector of the disease, global warming and the lack of appropriate policies to combat the vector insect, the risk of spread of the disease in urban areas cannot be neglected. The chaos caused by dengue in the state of Rio de Janeiro, which by the way is transmitted by the same vector of Yellow Fever, illustrates the risk of a possible (but not likely) outbreak of urban Yellow Fever in the country. Considering all these factors, the development of a complementary vaccine strategy, and/or alternative against Yellow Fever, can complement/replace the use of attenuated virus vaccine version.

Although no DNA vaccine has been approved for human use, this type of technology has been increasingly enhanced and potentially shall replace the formulations based on living microorganisms. DNA-based formulations can be easily handled and dosed, require no special temperature condition for storage and distribution and even eliminate any possible risk of infection by the live/attenuated agents. This type of technology also allows the handling of immunogens able to stimulate the immune system with specific epitopes and biological signals, avoiding the use of unnecessary and potentially harmful antigens/epitopes regarding to possible cross-immune responses (main obstacle to the development of an effective vaccine against dengue, due to cross-reaction between its 4 serotypes). Finally, with the technological advancements of tools for manipulation of microorganisms and purification of molecules on a large scale, DNA vaccines might be produced on a larger scale and with a lower final cost when compared to the attenuated/inactivated formulations.

It is important to note that before the encouraging significantly results obtained by our group, using a genetic vaccine based on the viral sequence of the E protein fused to the LAMP, and improving this vaccine by the optimization of antigens for the expression in humans, we believe in the possibility of developing and implementation of a DNA vaccine, even more secure, able to confer immunity against the virus of Yellow Fever in humans. This type of technology might also serve as subsidy to the development of other viral vaccines, especially against other flaviviruses such as Dengue virus.

SUMMARY OF THE INVENTION

The present invention, in its broadest aspect, is directed to an optimized DNA vaccine based on the region encoding the envelope of the Yellow Fever virus fused to the Association Protein to the Lysosomal Membrane—LAMP, able to process the encoded antigen and present it to the immune system via MHC II.

BRIEF DESCRIPTION OF THE FIGURES AND TABLES

The patent or application file contains at least one drawing executed in color. Copies of this patent or patent application publication with color drawing(s) will be provided by the Office upon request and payment of the necessary fee.

FIG. 1: Schematic of the annealing regions for the amplification of Wild PreM/M-E (for YFE) and PreM/M-E fused to the LAMP (pL/YFE). Scheme represented the entire genome of the virus of Yellow Fever, composed of 3 structural genes [Capsid (C), Membrane (PreM/M) and Envelope (E)] and 7 nonstructural (NS1-NS5). The black arrows indicate the annealing regions of the primers (Oligonucleotides) used for the amplification of wild PreM/M-E (carboxy-terminal region of the capsid X transmembrane region C-terminal of the envelope). For the amplification of PreM/M-E, for the fusion with LAMP, "reverse" primer used was designed to yearn before the transmembrane region of the envelope (white arrow).

Figure 2:
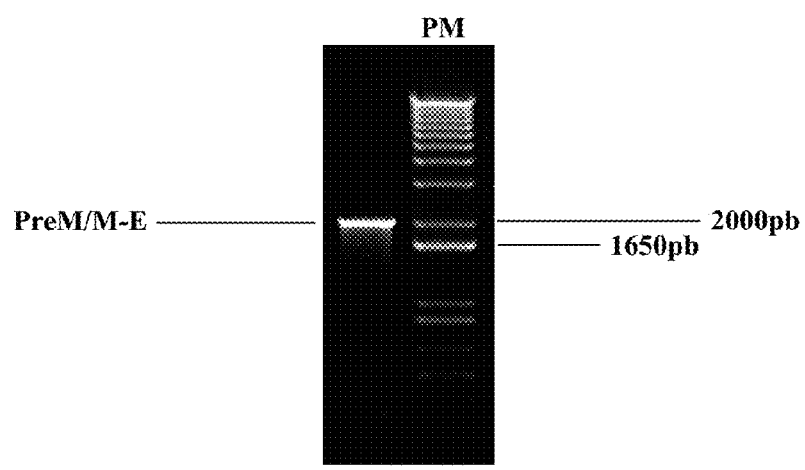

FIG. 2: PCR PreM/M-E product of the YF virus. After the amplification by PCR, using primers designed to the wild PreM/M-E sequence (Table 1) was obtained a fragment of approximately 2000 pb as expected. The referred PCR product was migrated in 1% agarose gel and visualized to the transluminator of ultraviolet light. The 1 kb plus ladder (Invitrogen®) was used as molecular weight marker (MW), indicating as reference to the 1650 and 2000 base pairs bands.

Figure 3:
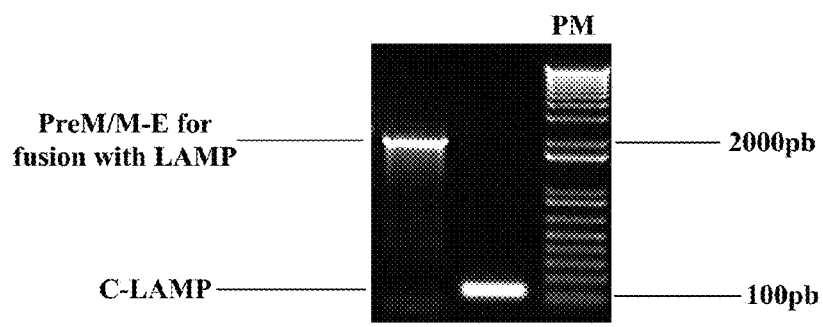

FIG. 3: PCR PreM/M-E products of YFV for fusion with LAMP and C-LAMP (human). After amplification by PCR, using primers designed for the PreM/M-E sequences for the fusion with LAMP and human C-LAMP (Table 1), a fragment of approximately 1900 bp (PreM/M-E) and other of 125 bp (C-LAMP) were obtained as expected. These PCR products were migrated in 1% agarose gel and visualized to the ultraviolet light transluminator. 1 kb plus ladder (Invitrogen®) was used as molecular weight marker (MW), indicated as reference to the 100 and 2000 base pairs bands.

Figure 4:
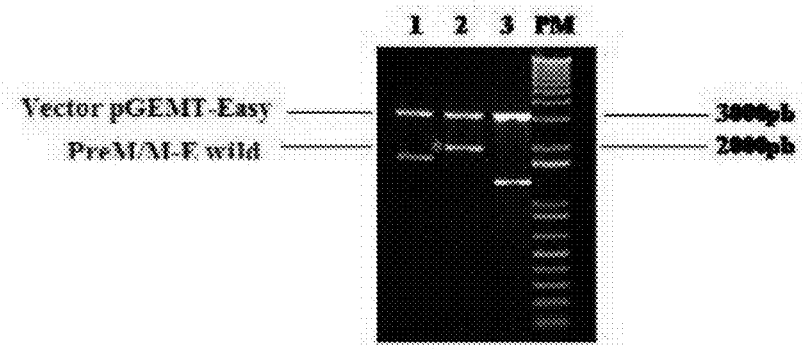

FIG. 4: Digestion of plasmid DNA to confirm cloning of the wild PreM/M-E sequence on the pGEMT-Easy vector. After transformation with the connection pGEMT-Easy+wild PreM/M-E, 3 white bacterial clones (screened by IPTG/X-Gal) were inoculated in liquid medium for subsequent extraction of plasmid DNA. The obtained minipreps were then digested with the XhoI and NotI enzymes to confirm the cloning of wild PreM/M-E in the pGEMT-Easy vector. The digestion products were then migrated in 1% agarose gel and visualized by ultraviolet light transluminator. 1 kb plus ladder (Invitrogen®) was used as molecular weight marker (MW), indicated as reference of 3000 and 2000 base pairs bands. Only clone 2, asterisk, released a fragment of the expected size (2000 pb).

Figure 5:
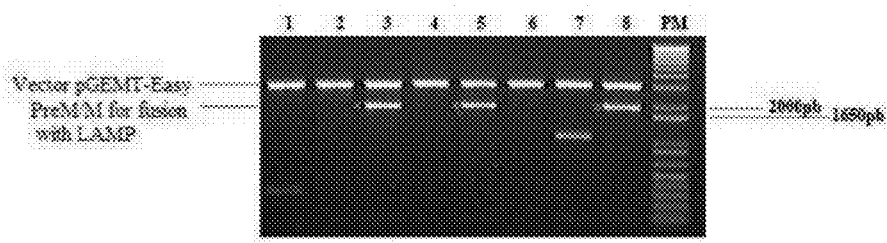

FIG. 5: Digestion of plasmid DNA to confirm cloning of the PreM/M-E sequence for fusion with LAMP in the pGEMT-Easy vector. After transformation with the connection pGEMT-Easy+PreM/ME for fusion with LAMP, 8 white bacterial clones (sorted by the IPTG/X-Gal) were inoculated in liquid medium for subsequent extraction of plasmid DNA. The obtained minipreps were then digested with the NheI and XhoI enzymes to confirm the cloning of PreM/M-E for fusion with LAMP in the pGEMT-Easy vector. The digestion products were then migrated in 1% agarose gel and visualized by ultraviolet light transluminator. 1 kb plus ladder (Invitrogen®) was used as molecular weight marker (MW), indicated as reference the 1650 and 2000 bp bands. The clones 3, 5 and 8 (asterisks) released fragments of the expected size (1900 pb).

Figure 6:
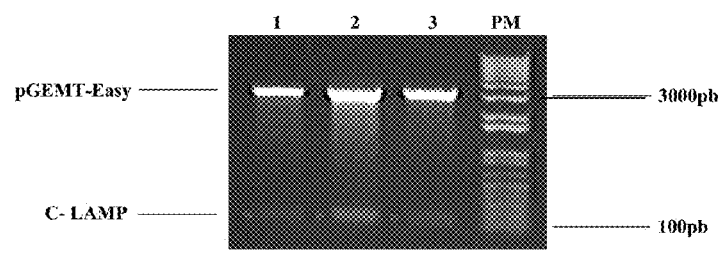

FIG. 6: Digestion of plasmid DNA to confirm cloning of C-LAMP in the pGEMT-Easy vector. After transformation with the connection pGEMT-Easy+C-LAMP, 3 bacterial clones were inoculated in liquid medium for subsequent extraction of plasmid DNA. The obtained minipreps were then digested with the XhoI and XbaI enzymes to confirm the cloning of C-LAMP in the pGEMT-Easy vector. The digestion products were then migrated in 1% agarose gel and visualized by ultraviolet light transluminator. 1 kb plus ladder (Invitrogen®) was used as molecular weight marker (MW), indicated as reference the 100 and 3000 base pairs bands. Out of the total 3 clones, all released the fragments of the expected size (125 bp, asterisks).

Figure 7:
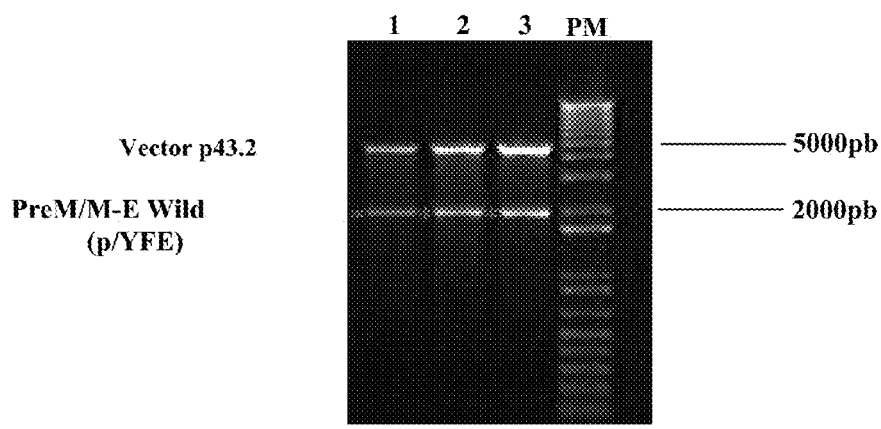

FIG. 7: Digestion of plasmid DNA to confirm the cloning of the wild PreM/M-E sequence in the p43.2 vector. After transformation with the connection p43.2+wild PreM/M-E, 3 bacterial clones were inoculated in liquid medium for subsequent extraction of plasmid DNA. The obtained minipreps were then digested with the XhoI and NotI enzymes to confirm the cloning of wild PreM/M-E in the p43.2 (p/YFE)

vector. The digestion products were then migrated in 1% agarose gel and visualized by ultraviolet light transluminator. 1 kb plus ladder (Invitrogen®) was used as molecular weight marker (MW), indicated as reference the 2000 and 5000 bp bands. All the clones released fragments of the expected size (2000 bp, asterisks).

Figure 8:
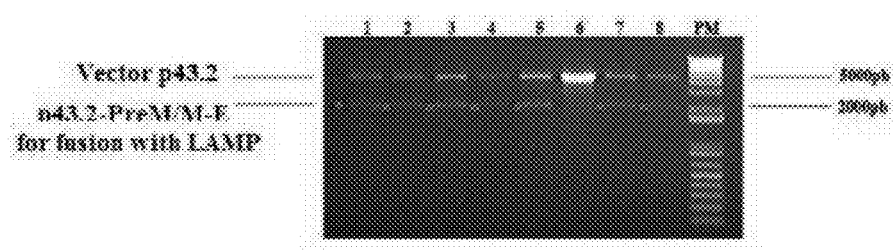

FIG. 8: Digestion of plasmid DNA to confirm cloning of the p43.2–PreM/ME sequence for fusion with LAMP in the p43.2 vector. After transformation with the connection p43.2+PreM/M-E for fusion with LAMP, 8 bacterial clones were inoculated in liquid medium for subsequent extraction of plasmid DNA. The obtained minipreps were then digested with the NheI and XhoI enzymes in order to confirm the cloning of p43.2–PreM/M-E for fusion with LAMP in the p43.2 vector. The digestion products were then migrated in 1% agarose gel and visualized by ultraviolet light transluminator. 1 kb plus ladder (Invitrogen®) was used as molecular weight marker (MW), indicated as reference the 2000 and 5000 bp bands. Out of the total of 8 clones, 7 released fragments of the expected size (1900 bp, asterisks).

Figure 9:
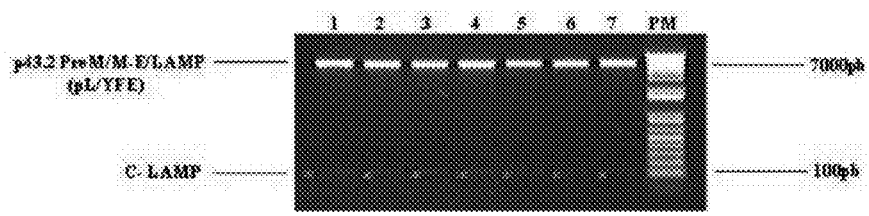

FIG. 9: Digestion of plasmid DNA to confirm cloning of C-LAMP in the p43.2–PreM/ME vector for fusion with LAMP. After transformation with the connection p43.2–PreM/ME+C-LAMP, 7 bacterial clones were inoculated in liquid medium for subsequent extraction of plasmid DNA. The obtained minipreps were then digested with the XhoI and XbaI enzymes to confirm the cloning of C-LAMP in the p43.2–PreM/ME/LAMP (pL/YFE) vector. The digestion products were then migrated in 1% agarose gel and visualized by ultraviolet light transluminator. 1 kb plus ladder (Invitrogen®) was used as molecular weight marker (MW), indicated as reference the 100 and 7000 base pairs bands. Out of total of 7 clones, all released the fragments of the expected size (125 bp, asterisks).

Figure 10:
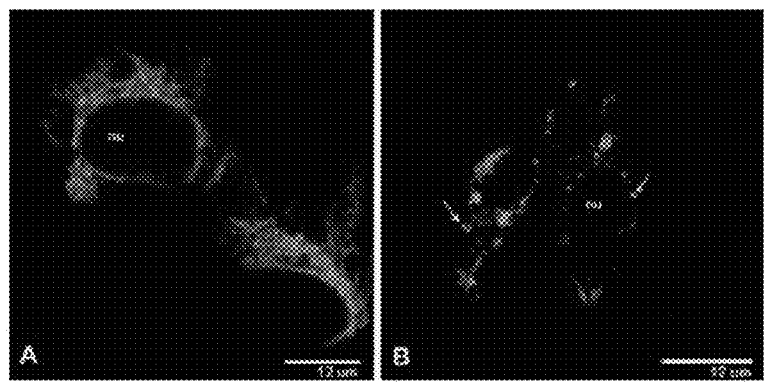

FIG. 10: Cells 293 transfected with the constructions p/YFE to pL/YFE. Validation of the expression of proteins encoded by plasmids p/YFE and pL/YFE, as well as the intracellular localization thereof, was carried out by immunofluorescence assay. Both E protein and E/LAMP were detected using polyclonal antibody, anti-YFV. The expected distribution of the wild E viral protein, typically associated with reticular membrane, was confirmed (A). In addition, the chimeric protein E/LAMP (present in cells 293 transfected with pL/YFE) presented distributed by the reticular membrane more particularly associated with the lysosomal membranes (as was also expected due to the presence of LAMP).

Figure 11:
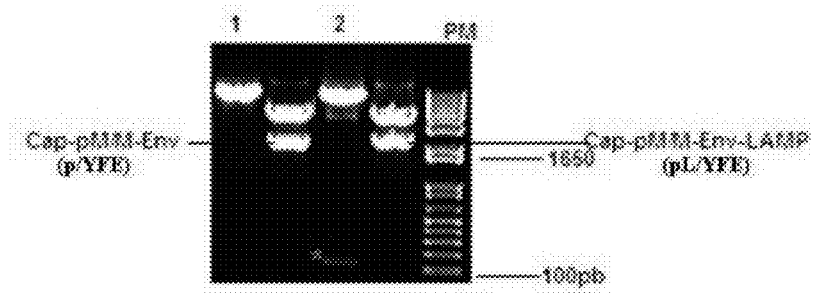

FIG. 11: Digestion of plasmid DNA, in endotoxin-free conditions, to confirm the identity of the vectors (p/YFE and pL/YFE). After transformation with constructions p/YFE and pL/YFE, isolated colonies of each construction were inoculated into liquid medium for subsequent extraction of plasmid DNA. The obtained Gigapreps were then digested. The construction of wild (w/YFE) was subjected to two digestion tests. The first with the XhoI and XbaI enzymes, in which there was linearization of construction (1) and with the XhoI and NotI enzymes that generated the release of the fragment encoded by p/YFE. The construction with LAMP (pL/YFE) was also subjected to two digestion tests. The first with the XhoI and XbaI enzymes, in which there was release of LAMP (asterisk), and with the NheI and XbaI enzymes which generated the releasing of the fragment coded by pL/YFE. The digestion products were migrated in 1% agarose gel and visualized by ultraviolet light transluminator. 1 kb plus ladder (Invitrogen®) was used as molecular weight marker (MW), indicated as reference the 1650 and 100 base pairs bands.

Figure 12:
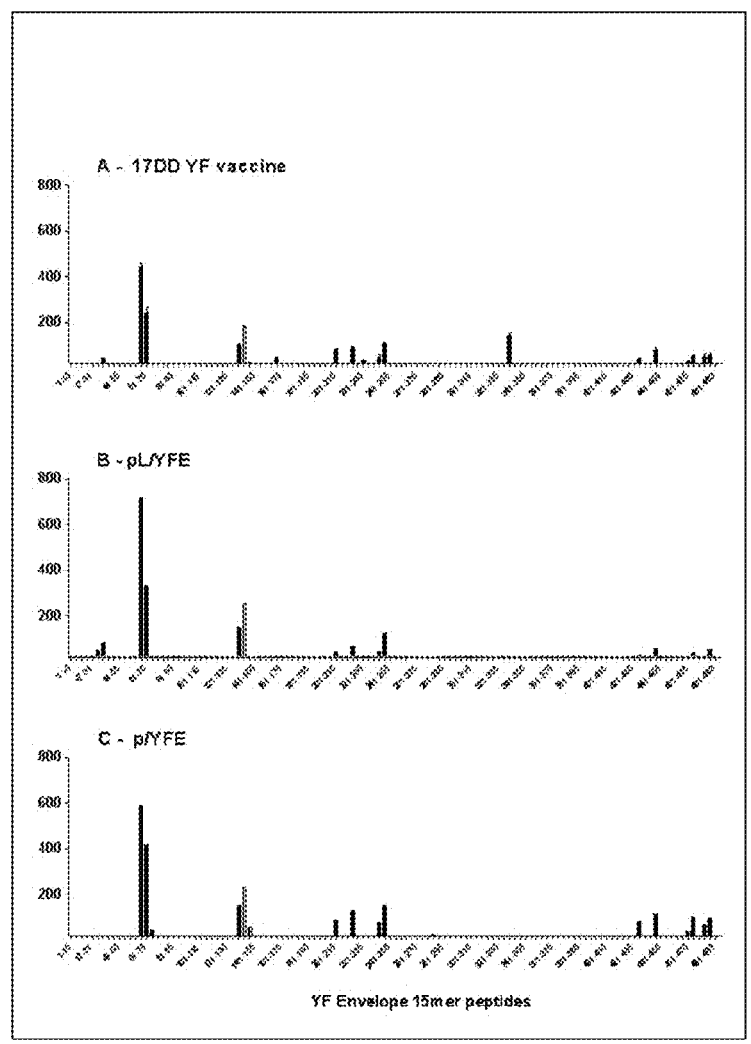

FIG. 12: Comparison of induced cellular responses in Balb/C mice, using the 17DD vaccine and the constructions p/YFE and pL/YFE. Balb/C mice were immunized on days 0 and 21 with: (A) $10^4$ Colony Forming Units—PFU of the 17DD vaccine, (B) 50 ug of the pL/YFE vaccine or (C) 50 ug of the p/YFE vaccine. 7 to 10 days after the last immunization splenocytes samples of the mice were isolated for testing the ELISPOT—IFN-γ, using a library of synthetic peptides, amino acids each with "overlapping" of 11 amino acids between them, covering the entire E protein of YFV. This figure represents an average of 2-4 experiments performed with "pools" of 3-5 mice each.

Figure 13:
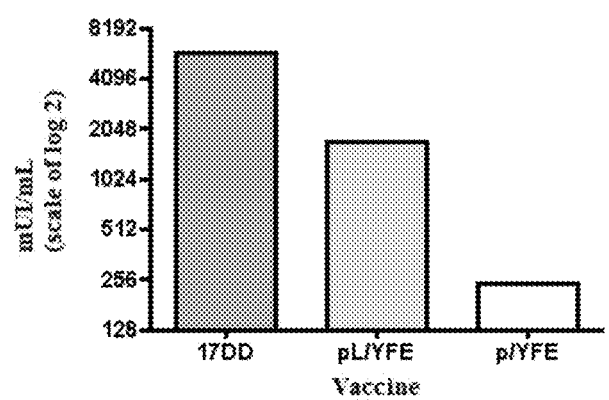

FIG. 13: Neutralizing antibody levels detected in BALB/c and C57Bl/6 mice, after immunization with 17DD, pL/YFE and p/YFE vaccines. Mice of both species were immunized with conventional or DNA vaccines on days 0, 30 and 45 and its immune sera were obtained on days 15, 45 and 60. Sera were tested individually by plaques reduction neutralization—PRNT, compared with monkey serum containing neutralizing antibodies against YFV in a known concentration. The construction pL/YFE, although inducing the production of neutralizing antibodies approximately 3.5 times smaller than the 17DD vaccine, is capable of inducing neutralizing antibody titers at least 7 times higher than the titers induced by p/YFE.

Figure 14:
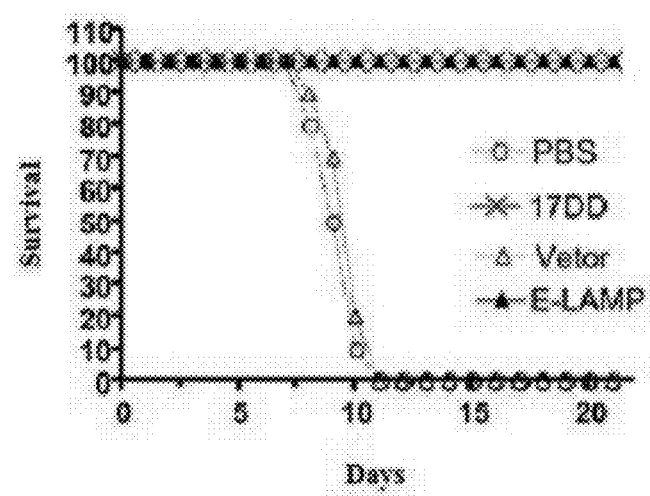

FIG. 14: Evaluation of protection against YFV, through intracerebral injection testing in mice previously immunized with 17DD and pL/YFE. The protection assays were performed using the model of immunization/challenge, by injecting $10^5$ PFU of the 17DD vaccine virus (intracerebrally) in mice previously immunized with the 17DD vaccine and with pL/YFE vaccine. Animals were immunized 3 times (days 0, 30 and 45) and challenged 15 days after the last immunization. Both the 17DD vaccine and the pL/YFE vaccine were able to protect 100% of the challenged animals. Table 2 adds the information of this figure, regarding to the number of challenged animals, as well as comparing the efficiency of DNA vaccines in both species.

Table 1: Oligonucleotides (primers) used to generate the vaccine constructions p/YFE and pL/YFE. For the design of nucleotide capable of amplifying the wild PreM/M-E and PreM/M-E-LAMP sequences was used the public domain software Ape [developed by Dr. M. Wayne Davis—(http://www.biology.utah.edu/jorgensen/wayned/ape/)].

Table 2: Results of protection test in BALB/c and C57B1/6 mice compared with the 17DD vaccine with DNA pL/YFE vaccine. Mice immunized with 17DD vaccine, and with the DNA pL/YFE construction were challenged intracerebrally with the YFV 17DD. Both lineages of mice were 100% protected by the conventional vaccine and DNA vaccine. As a negative control, mice underwent the same immunization schemes with the empty p43.2 vector and PBS.

Table 3: Comparison of expression levels of the envelope proteins of Yellow Fever, wild and optimized, by flow cytometry. Cells 293 were transfected with 1 ug of each DNA vaccine, using lipofectamine, and stained with anti-envelope rabbit serum of Yellow Fever. Transfection of the cells was normalized, using as an internal control a plasmid encoding a fluorescent protein, and in relation to the level of expression of the protein encoded by the encoding construction of the native sequence of the envelope (number 2). The plasmid optimized (number 6) showed an expression level 6.5 times higher than the plasmid encoding the native sequence (number 2).

DETAILED DESCRIPTION OF THE INVENTION

The present inventors have developed and evaluated the expression efficiency and ability to induce the immune response of two genetic vaccines, both based on the strategy of co-expression of the proteins PreM/M and E of YFV (one wild and the other fused to the LAMP). Both constructions, wild (p/YFE) and with LAMP (pL/YFE), were used to transfect human cell and the respective proteins encoded by them were detected by immunofluorescence. Then the vectors p/YFE and pL/YFE were inoculated into mice and the immune responses, induced by each construction, were analyzed in terms of cellular and humoral responses. Results were considered excellent since the two constructions are capable of inducing T cell response against the same epitopes induced by the 17DD vaccine, and PL/YFE was also able to induce high titers of neutralizing antibodies. These vectors were also inoculated into mice then were challenged against YFV, in order to assess whether these constructs are able to protect these animals against FA. Despite the construction pL/YFE have been able to generate higher neutralizing antibody titers than the wild construction p/YFE in both Balb/c as in immunized C57Bl/6, both constructions conferred 100% of protection to the mice challenged. These results are considered excellent.

The vaccine pL/YFE was further optimized, generating the construction pL/YFEopt, using the genetic algorithm of the LETO 1.0 (Entelechon®) program. Factors were taken into consideration in the optimization process, such as: codon usage, mRNA secondary structure, presence of repetitive DNA motives, GC content, presence/absence of restriction sites, cryptic sites of "splicing", etc. The optimized sequences were sent to the commercial synthesis (Geneart®) and then sub cloned into the vector 8L, wild and with LAMP. The optimized vaccine constructions, as well as wild p/YFE and pL/YFE, will be inoculated into conventional and transgenic mice (expressing human HLAs) and evaluated for its immunogenicity using ELISPOT assays, virus neutralization by plaque reduction (PRNT) and defiance against YFV.

The invention will be now described using examples. The following examples are illustrative of the invention and represent preferred embodiments, those skilled in the art know or are able to find, using nothing more than routine experimentation, how to use other materials and appropriate techniques.

PCR Amplification

The primers designed (Table 1) for the amplification of wild PreM/M-E, PreM/M-E for fusion with LAMP and C-terminal domain of LAMP, allow the obtaining of the respective sequences with the expected molecular weights. The wild sequence PreM/M-E was amplified using primers flanking the N-terminal region of PreM/M (more specifically at the level of the carboxy-terminal region of the capsid) and the C-terminal trans membrane region of the envelope. For the amplification of the PreM/M-E sequence, aiming to merge the C-terminal domain of LAMP, the "forward" primer used was designed to ring with the same region of the capsid. Moreover, the used "reverse" primer was designed to more internally ring within the region that encodes the envelope. Thus, the sequence PreM/M-E (for fusion with LAMP) lacks the C-terminal trans membrane domain of the envelope, aiming at its replacement by the C-terminal domain of LAMP (FIG. 1).

The PCR product PreM/M-E for fusion with LAMP has approximately the same size of the wild PreM/M-E product, as the region removed from the envelope has only 100 base pairs (bp). To replace this C-terminal trans membrane domain of the envelope, we design primers capable of amplifying the C-terminal region of LAMP-1 human (C-LAMP). The "forward" primer allows the merger (in phase) of PreM/M-E with C-LAMP, while the "reverse" primer has the translation termination codon. The PCR product of the wild PreM/M-E sequence, approximately 2000 base pairs (bp), can be seen in FIG. 2. PCR products, PreM/ME for fusion with LAMP (1900 bp) and C-LAMP (125 bp), can be seen in FIG. 3.

Cloning of PCR Products Obtained in the pGEMT-Easy Vector

Once confirmed the expected sizes of the wild PCR PreM/ME products, PreM/M-E for fusion with LAMP and C-LAMP, these were cloned in the pGEMT-Easy vector. To facilitate screening of positive clones, clones containing the insert inserted into the lacZ fragment of β-galactosidase gene, only white clones of each construction were selected. 3 clones were selected from the plate containing the bacteria transformed with the connection pGEMT-Easy+wild PreM/ME. These clones were inoculated in growth liquid medium for subsequent preparation of plasmid DNA (miniprep) and digestion proof to confirm the cloning. Out of the 3 selected clones only 1 released of the expected insert of 2000 bp on the construction of wild PreM/M-E (FIG. 4). Regarding the connection pGEMT-Easy+PreM/ME for fusion with LAMP, 8 white clones were selected. These clones were also subjected to plasmid extraction and digestion proof. Out of the 8 selected clones, 3 released the insert of 1900 expected, relative to the construction PreM/M-E for fusion with LAMP (FIG. 5). 3 clones were selected from the connection pGEMT-Easy+C-LAMP, all of which released the insert after digestion (FIG. 6).

Sub Cloning of the Fragments Cloned in the pGEMT-Easy in the Vector p43.2

For the sub cloning of PreM/M-E in the p43.2 vector, this fragment was cleaved from pGEMT-Easy vector and inserted into p43.2 vector. To facilitate screening of positive clones, 3 different concentrations of insert were connected in a p43.2 vector constant concentration (a connecting in the absence of insert was performed as negative control). Thus the plate was selected with the highest number of clones, comparing the plates with different concentrations of insert with the negative control for the selection of clones. 3 clones were selected from this plate containing bacteria transformed with the connection p43.2+wild PreM/M-E. These clones were inoculated in growth liquid medium for subsequent preparation of plasmid DNA and digestion proof to confirm the cloning. Out of the 3 selected clones all released the insert of expected 2000 bp on the construction p/YFE (FIG. 7). Regarding the construction p43.2+PreM/M-E/LAMP an intermediate vector was necessary to construct, containing PreM/M-E for the fusion with lamp, for the subsequent fusion of LAMP. Thus, the PreM/M-E fragment for the fusion with LAMP was cleaved from the pGEMT-Easy vector and sub cloned in the p43.2 vector, generating the intermediate construction p43.2–PreM/M-E for the fusion with LAMP. 8 clones were selected from this connection, of which 7 have released the insert of 1900 bp expected after the digestion proof (FIG. 8). To fuse LAMP to the fragment p43.2–PreM/ME for fusion with LAMP, C-LAMP was cleaved of the pGEMT-Easy/C-LAMP vector and purified. Then the p43.2–pM/ME vector for fusion with LAMP was cleaved with the same enzymes, allowing the insertion of LAMP in its C-terminal, generating the construction pL/YFE. To confirm the insertion of lamp LAMP in the p43.2–PreM/ME to fusion with LAMP, 7 clones were digested of which all released the fragment of expected 125PB (FIG. 9).

Sequencing of the Constructions p/YFE and pL/YFE

To confirm the identity and quality of the sequences sub cloned in p43.2 vector, the respective vectors were sequenced using internal primers designed for yearning at each 400 bp of the cloned inserts (meaning "forward" and "reverse"). The obtained sequences were analyzed by the ApE® and Laser-gene® programs. In the construction p/YFE, 2 non-silent punctual mutations were found, i.e., which change the amino acid are in a total of 644 amino acids. The changes were from an alanine (A) to a valine (V) at position 250, and serine (S) to an aspartic acid (D) at the position 349. These mutations were also the only ones found in the construction pL/YFE, indicating that the mutations did not occur at the level of PCR but were already present in the DNA template used for amplification. Considering the E protein has several epitopes for B cells (because only the E and NS1 protein are capable of generating neutralizing antibodies), as well as T cells (data not shown, obtained by employees of our group), these mutations were considered irrelevant to our study of vaccine development.

Detection of Proteins E and E/LAMP by Immunofluorescence

To evaluate the expression of the proteins E and E/LAMP encoded by the constructions p/YFE and pL/YFE respectively, human cells 293 were transfected with these DNA vaccines. Despite the low efficiency of expression (about 40%), both proteins were detected in the appropriate cell compartment. As expected, it was confirmed the characteristic reticular distribution of the wild antigen E (FIG. 10A), as well as the characteristic lysosomal distribution of the E-LAMP protein FIG. 10B).

Evaluation of the Immune Response Induced in Mice Immunized with p/YFE and pL/YFE Vaccines.

For the immunization testing, the DNA vaccines, p/YFE and pL/YFE were initially prepared on a large scale free of endotoxins. The obtained preparations were submitted to digestion proofs with specific enzymes in order to ensure the quality/identity of the vectors. The p/YFE vector was digested with the XhoI and XbaI enzymes and XhoI and NotI enzymes, whereas the pL/YFE vector was digested with the XhoI and XbaI enzymes and NheI and XbaI enzymes. All digestions released DNA fragments in the expected size (FIG. 11). Next, the constructions p/YFE and pL/YFE were used for experimental tests of immunization in mice.

The p/YFE and pL/YFE plasmids, free of endotoxins, were then inoculated in BALB/c and C57Bl/6 mice, using as positive control and negative control the 17DD vaccine and saline solution negative controls and empty p43.2 vector. The immune responses, induced by each construction were analyzed in terms of cellular response (by testing "Enzyme-Linked Immunosorbent SPOT—ELISPOT") and humoral (by virus neutralization tests—PRNT). The obtained results were considered excellent because the two constructions are capable of inducing T cell response against the same epitopes induced by conventional attenuated virus vaccine (FIG. 12), and the construction pL/YFE was still capable of inducing neutralizing antibodies at a concentration considered quite satisfactory. The construction pL/YFE, although inducing a production of neutralizing antibodies approximately 3.5 times smaller than the 17DD vaccine, is capable of inducing neutralizing antibody titers at least seven times higher than p/YFE (FIG. 13).

The pL/YFE vector was then inoculated 3 times (50 μg/immunization) in BALB/c and C57BL/6 mice. Again, 17DD vaccine was used as positive control, and both the empty p43.2 vector and saline solution (1×PBS) were used as negative controls. Two weeks after the last immunization, the animals were challenged by inoculation against YFV by the inoculum of $10^5$ Plaques Forming Units (PFU) of the 17DD vaccine (intracerebrally). The 17DD vaccine and the DNA pL/YFE (E-LAMP) vaccine conferred 100% protection to challenged mice (FIG. 14 and Table 2).

Optimization of the pL/YFE Vaccine Generating Constructions pL/YFEopt1 and pL/YFEopt2.

To improve the efficiency of E antigen expression in eukaryotic cells, aiming at the experiment in primates, the DNA sequence encoding the E protein was optimized. This sequence was analyzed/optimized with respect to features such as "codon usage", secondary structure of messenger RNA (mRNA), distribution of the GC content, DNA repetitive motions, restriction sites, "splicing" cryptic sites, etc. The optimization process takes into account the various parameters mentioned above, while seeking a balance between them.

Two optimized versions were generated of the pL/YFE vaccine, called pL/YFEopt1 and pL/YFEopt2. The optimized constructions were then used to transfect human cells 293, with the objective of evaluating the expression efficiency of optimized E-LAMP antigen (E-LAMP$_{OPT1-2}$) with respect to wild E-LAMP antigen. By immunofluorescence assay, the expression of E-LAMP was considered at least 20 times greater (data not shown). Although, quantitative assays of "Western blot" have not been performed to evaluate, more accurately, how many times E-LAMPOPT1 are more expressed in relation to wild E-LAMP, we can say that the expression of these E-LAMPOPT1 antigens is significantly superior to the wild antigen expression.

Considering the greater efficiency of p43.2/E-LAMP$_{OPT1-2}$ expression relative to wild p43.2/E-LAMP, we believe that possibly the optimized DNA vaccine is deemed to be even more efficient than the wild vaccine previously tested. The higher efficiency of expression is likely to be accompanied by a higher neutralizing antibody titer, increasing the potential of the optimized vaccine with respect to the number of doses and concentration of DNA in each dose. Although p43.2 vector have been optimized for the expression in eukaryotic cells (by combining specific promoters, transcription factors, signal sequences for polyadenylation, resistance markers, etc.), some DNA sequences contained therein (such as for example that one encoding the ampicillin resistance mark) are not allowed by "Food and Drug Administration-FDA" for use in humans. On the other hand, other expression vectors, such as the 8L vector, for example, do not present these undesirable sequences and, therefore, are not restricted by the FDA. Thus, the E-LAMP$_{OPT1-2}$ antigens were still cloned in the 8L vector generating the p8L/E-LAMP$_{OPT1-2}$ constructions that will be initially evaluated in mice, and later in monkeys.

Example 1

Construction of the Transfection Vectors:
p43.2–PreM/M-E (p/YFE) and
p43.2–PreM/M-E-LAMP (pL/YFE)

1.1—Amplification and Purification of PCR Products

The PreM/M-E sequence of YFV, including the carboxy-terminal sequence of the capsid (responsible for the translocation of PreM/M to the endoplasmic reticulum) was amplified by PCR, from a plasmid containing the entire genome of the YFV [infectious clone kindly provided by Dr. Ricardo Galler (Biomanguinhos-IOC/FIOCRUZ)]. PreM/M-E was amplified with two separate pairs of primers for obtaining the wild sequence (extending from the nucleotide 392 until the nucleotide 2452 of the genome of Yellow Fever, based on the sequence of accession number NC 002031 in the Genbank—NCBI), as well as from a sequence of fusion incorporating LAMP in the carboxy-terminal region (extending from the nucleotide 392 to the nucleotide 2323 of the genome of Yellow Fever, based on the sequence of access number NC 002031 in the Genbank—NCBI). The C-terminal sequence of LAMP was amplified from a plasmid containing the N-terminal and C-terminus regions of LAMP-1 human, p43.2 hLAMP/GAG [kindly provided from Dr. Ernesto Marques (LaViTE-CPqAM/FIOCRUZ)]. Specific primers were used that allowed the incorporation of: specific restriction sites, translation initiation ATG codon (in context with the Kozak sequence) and termination codon of the translation (see Table 1). PCR reactions were performed in final volume of 50 μL containing: 1× buffer Tgo (Roche®); 0.2 mM dNTP (Invitrogen®); 0.6 uM of each primer; 1 unit of the polymerase DNA Tgo enzyme (Roche®); 10 ng of template DNA. The samples were amplified in a Mastercycler gradient (Eppendorf®) thermocycler programmed as follows: 1—94° C. for 2 min (denaturation); 2—[94° C. for 1 minute (denaturation); 55° C. for 30 seconds (yearning); 68° C. for 75 seconds (extension)-30 cycles (amplification)] 3—68° C. for 10 minutes (extension and completion of incomplete fragments). The PCR products were migrated on agarose gel for subsequent purification using the QIAEX II commercial kit (Qiagen®), according to the manufacturer's recommendations.

1.2—Cloning of the PCR Products in Replication Vector

The purified PCR products were then subjected to treatment with the Taq DNA polymerase (Invitrogen®) enzyme, for adding adenines free in their ends. This reaction was performed in a final volume of 10 μL containing: 1×Taq polymerase buffer (Invitrogen®); 1.5 mM MgCl$_2$; 2 mM dATP (Invitrogen®); 5 Taq DNA polymerase units (Invitrogen®); 5 μL of the purified PCR product. The samples were incubated at 72° C., during 20 minutes in a Mastercycler Gradient (Eppendorf®) thermocycler. After treatment with Taq DNA polymerase (Invitrogen®), adenylate PCR products were used for cloning in pGEMT-easy (Promega®) vector. The connection reactions were performed using the pGEMT-Easy vector system I kit (Promega®) in a final volume of 10 μL containing: 1× buffer "Rapid Ligation"; 50 ng of the pGEMT-Easy vector; 0.4 units of T4 DNA ligase; 2 μL of treated PCR products. The connection reaction was performed at 4° C. for about 15 hours. Connections were then used to transform competent cells in order to confirm the cloning. Transformations were performed in a final volume of 80 μL containing: 50 μL of competent cells (*Escherichia coli* TG1); 25 uL of transformation buffer (5 mM MgCl2; 5 mM Tris-HCl pH 7.4); 5 μL of each connection product. The transformation reactions were incubated for 30 minutes on ice, and then subjected to thermal shock (37° C.—5 minutes) and cooled again on ice. The cells were seeded on plates with solid culture medium Luria-Bertani (LB), containing ampicillin in 50 μg/mL concentration and IPTG/X-Gal (10 mM IPTG; 0.1 mg X-Gal). The plates were incubated, for approximately 15 hours at 37° C., and then incubated at 4° C. for 1 hour to facilitate discriminating between empty clones (blue) and clones containing the insert (white).

1.3—Preparation of Plasmid DNA

In order to confirm the cloning, white colonies were selected, from each connection, for preparing plasmid DNA and digestion proof. The colonies were inoculated in 2 mL of liquid LB medium, containing ampicillin (50 μg/mL), and grown for approximately 15 hours at 37° C. Then 1.5 mL of each culture was centrifuged (13,200 rpm—5 minutes) to obtain bacterial sediment. The extraction of plasmid DNA was performed from these "pellets" using the QIAprep spin miniprep kit (Qiagen®), according to the manufacturer's recommendations. The plasmid DNAs, 50 μL each, was then used for the confirmation of cloning by the digestion tests.

The digestion reactions were performed in a final volume of 10 μL containing: 1× digestion buffer; 1.5 μL plasmid DNA. All digestions were carried out at 37° C. for about 4 hours. The pGEMT-Easy vector containing the PreM/M-E fragment was digested with 0.01 units of XhoI enzyme and 0.01 units of NotI enzyme. The pGEMT-Easy vector, containing the same sequence, but with different restriction site allowing the subsequent insertion of LAMP, was digested with 0.005 units of NheI enzyme and 0.01 units of XhoI enzyme. Since the pGEMT-Easy vector containing the C-LAMP fragment was digested with 0.01 units of the XhoI enzyme and 0.01 units of the XbaI enzyme. From the results of the digestion, verified on agarose gel, positive clones of each construction was digested on a large scale for further purification of the fragments. The digestion reactions on large scale were carried out in a final volume of 50 μL containing: 1× digestion buffer; 15 μL of plasmid DNA. All digestions were carried out at 37° C. for about 4 hours. The pGEMT-Easy vector containing the PreM/M-E fragment was digested with 0.1 units of XhoI enzyme and 0.05 units of NotI enzyme. The pGEMT-Easy vector containing the PreM/M-E fragment for fusion with LAMP was digested with 0.05 units of the NheI enzyme and 0.1 units of XhoI enzyme and the pGEMT-Easy vector containing the C-LAMP fragment was digested with 0.1 units of XhoI enzyme and 0.1 units of the XbaI enzyme. Then each fragment was purified by extraction of agarose gel, using the QIAEX kit II Gel Extraction Kit (Qiagen®).

1.4—Sub Cloning Wild PreM/M-E and PreM/M-E-LAMP in the p43.2 Vector

The p43.2 vector was subjected to digestion reactions to create restriction sites, compatible with the sites of the wild PreM/M-E and PreM/M-E fragments for the fusion with LAMP. The digestion reactions were carried out in two steps, first with an enzyme and then with other. For the cloning of wild PreM/M-E (p/YFE), the first digestion reaction was carried out in a final volume of 50 μL containing: 1× digestion buffer; 15 μL of the sample of vector and 0.05 U of the NotI (Biolabs®) enzyme. Digestion was performed at 37° C., for about 4 hours. After the digestion, it was verified whether the linearization of the vector occurred by comparing the size between the digested sample and the intact vector, both migrated under the same conditions on agarose gel. Verified the linearization, the sample was precipitated with ethanol and resuspended in a final volume of 40 μL. The second digestion reaction was carried out in a final volume of 50 μL containing: 1× digestion buffer; 40 μL of the vector sample and 0.1 units of XhoI enzyme. As for the cloning of PreM/M-E for the fusion with LAMP, the p43.2 vector was subjected to a digestion scheme, very similar to that used for cloning the wild fragment, and using the NheI and XhoI enzymes. The digestions were performed at 37° C. for approximately 6 hours. The reactions connection of both fragments, to the p43.2 vector, was carried out in a final volume of 10 μL containing: 1×T4 DNA ligase buffer (New England Biolabs®); 100 ng of p43.2 vector (cleaved with XhoI/NotI or NheI/XhoI); 0.4 units of T4 DNA ligase (New England Biolabs®); 3 μL of each purified fragment. The connection reactions were performed at 16° C. for about 20 hours. Connections were then used to transform competent cells in order to confirm the cloning. The procedures of transformation, preparation and digestion of plasmid DNA were the same as described above. Finally, for the insertion of the C-terminal fragment of LAMP (C-LAMP), in the p43.2–PreM/M-E vector for the fusion with LAMP, both the vector and the fragment C-LAMP were digested with the XhoI and XbaI enzymes (to obtain the construction pL/YFE).

1.5—DNA Sequencing

The buildings p/YFE and pL/YFE were subjected to the automatic sequencing for the certification of identity/quality of the cloned sequences. The sequencing reaction was performed in a final volume of 10 µL containing: 1× buffer "Save money" (200 mM Tris-HCl/pH 9.0, 5 mM $MgCl_2$); 0.32 µM of each primer (a total of six internal primers); 0.5 µL of "Bigdye" solution (Applied Biosystems®); 200 ng of DNA. The samples were incubated at 95° C. for 5 minutes, in a Gene AMP PCR System 9700 (Applied Biosystems®) thermocycler, for denaturation. Then these samples were subjected to the following cycles of PCR for sequencing: 1—94° C. for 2 minutes (initial denaturation); 2—[94° C. for 15 seconds (denaturation); 50° C. for 10 seconds (yearning); 60° C. for 4 minutes (extension)—45 cycles]. The samples were precipitated in 65% isopropanol, washed with 60% ethanol and resuspended in 15 µL of formamide (Applied Biosystems 0). Samples were sequenced in Integrated Core technology (NIT) of the CPqAM, using the automatic sequencer of DNA ABI Prism 3100 (Applied Biosystems®) in accordance with previously established standards in this unit.

Example 2

Cultivation, Infection and Transfection of Eukaryotic Cells

Eukaryotic cells 293 were grown in DMEM (Invitrogen®) medium supplemented with: 10% fetal bovine serum (Gibco®); 1% penicillin/streptomycin (Gibco®); 1% L-glutamine (Sigma®). These cells were used for both assays of viral infection, and for the transfection experiments. After reaching an approximately 90% confluence, cells were infected with a viral extract of YFV in the concentration of $0.36×10^6$ Plaque Forming Units—PFU, kindly provided by Dr. Marli Tenório (CPqAM/LaViTE). For the infection, the cells were initially incubated with the pure YFV extract (1 hour/37° C./5% of $CO_2$) and then added complete DMEM medium for cell maintenance. The infected cells remained in the same conditions of incubation (37° C./5% of $CO_2$) for 48 hours, until they present the cytopathology effects caused by the viruses. For transfection tests, cells 293 were grown under the same above conditions. They were then incubated with 0.8 µg of each DNA (p/YFE and pL/YFE), using as a negative control the empty p43.2 and as positive control the reporter gene of the β-galactosidase. The transfection reactions were performed using the Lipofectamine 2000 (Invitrogen®) kit, following the manufacturer's recommendations. Transfected cells were incubated (48 hours/37° C./5% of $CO_2$) and processed for evaluation of transfection efficiency, by the activity of reporter gene expression. For the reaction of β-gal coloring, cells were initially washed in 1×PBS and fixed in solution 0.2% glutaraldehyde/PBS. Then, the fixed cells were incubated in a final volume of 1 mL of a solution containing: 20 mg of X-Gal; 0.005M of potassium ferriciamide; 0.005M of potassium ferriciamide; 0.002M of $MgCl_2$ in 1×PBS, for developing the coloring for β-gal activity.

Example 3

Transfection and Expression Analysis by Immunofluorescence

Cells 293 were grown on coverslips and transfected with the obtained vaccine constructions, using the Lipofectamine 2000 kit (Invitrogen Life Technologies®). The empty p43.2 vector was used as negative control. Transfections were performed in culture plates of 24 wells with 2.5 µg of each plasmid and 10 µl of lipofectamine, according to the manufacturer's instructions. The cells were incubated 48 hours and then fixed in 100% methanol at −20° C. for 5 minutes, blocked in 1% BSA/PBS solution for 30 minutes, and incubated with the anti-Yellow Fever polyclonal (produced in mice in the CPqAM vivarium) at a dilution of 1:200. It was used the anti-IgG secondary antibody of conjugated mouse to the fluocromo Alexa 488, produced in goat, at a dilution of 1:500 (Molecular Probes, Seattle, USA). Then, the coverslips were mounted on slides using the "Prolong gold" normal (Molecular Probes, Seattle, USA) and viewed by confocal microscopy. Images were obtained by Leica SPII-AOBS confocal microscope (Leica Microsystems, Hm®) using the 63×NA 3.1 objective lens immersed in immersion oil. The fluocromo Alexa 488 was excited using the laser Arkr at a wavelength of 488 nm and the digital image captured using the Leica software, in the 24-bit RGB format, in an area of 1024×1024 pixels. The capture fields were selected according to the dispersion and morphology of the cells.

Example 4

Evaluation of the Immune Response Induced in Mice Immunized with p/YFE and pL/YFE Vaccines 4.1—Acquisition of Large-Scale Vaccine Vectors The constructions encoding the wild viral E proteins (p/YFE) and protein E fused to the Lysosome-Associated Membrane Protein—LAMP (pL/YFE), were submitted to the preparation of plasmid DNA on a large scale. Aliquots of each DNA were used to transform competent cells (*E. coli* TG1). Then, a single colony from each plate was chosen to be inoculated in 12 ml of liquid LB medium, containing ampicillin (50 µg/ml), and grown for approximately 8 hours at 37° C. under vigorous stirring. After this time, each culture was inoculated in 2.5 liter of LB/ampicillin medium and grown at 37° C. for 16 hours under vigorous stirring. Then, the culture was centrifuged (8,000 RPM—15 minutes) to obtain the bacterial sediment. From this "pellet", it was performed the extraction of the plasmid DNA (endotoxin-free conditions) using the commercial kit, Endofree Plasmid Giga Kit (Qiagen®), according to manufacturer's recommendations. The plasmid DNAs were subjected to digestion tests in a final volume of 10 µL containing: 1× digestion buffer, 1 µL of each plasmid DNA and specific restriction enzyme. The digestions were performed at 37° C. for approximately 4 hours.

4.2—Animals and Immunization Protocols

For tests of neutralization and protection, BALB/c and C57B1/6 female mice with 3 weeks old were immunized on days 0, 30 and 45. One day before each immunization serum samples were collected from each animal. The mice were immunized at the tail base with the 17DD attenuated virus vaccine at $10^4$ PFU/50 µl (positive control), DNA p/YFE and pL/YFE vaccines (both in the concentration of 50 µg/50 µl), as well as with empty vector and PBS (negative controls). All procedures were performed in accordance with the requirements of the Ethics Committee on Animal Use (CEUA), according to the protocol P-0259-05 approved by this committee.

4.3—Plaque Neutralization Tests

For analysis of induced neutralizing antibody titers, by the vaccinations with 17DD and with the constructions p/YFE and pL/YFE, tests were performed for virus neutralization by plaques reduction (PRNT). These tests were performed using serum samples of Balb/c and C57BL/6 mice collected before and after vaccination. The neutralization tests were evaluated by reduction of the plaque formation of the Yellow Fever virus, grown in Vero cells. After inactivation of the serum (30 min/56° C.), serial dilutions of serum were incubated with 50-100 PFU of virus for 30 min at 37° C., and added in 6-well plates containing Vero cells. After 1 hour incubation, the inoculum was removed and added to semi-solid medium containing agarose. After 8 days incubation the plates were fixed, and the formation of viral plaques was detected by immune-peroxidase assay. The neutralization test by plaques reduction was defined by the dilution at which the number of plaques was reduced by 50%, PRNT50, when compared with the control.

4.4—Tests of Security Assessment

Balb/c and C57BL/6 mice immunized 3 times with the 17DD vaccine, or DNA vaccines, were used in protection tests. The animals were challenged by intracerebral inoculum, containing 10,000 PFU of 17DD virus, 15 days after the last immunization. The animals were monitored for 21 days to evaluate symptoms of neurovirulence and mortality. Dying animals were sacrificed by exposure to $CO_2$.

Example 5

Optimization of pL/YFE Vector Through the Genetic Algorithm

To improve the efficiency of expression of the antigen encoded by the pL/YFE vaccine in eukaryotic cells, aiming at future experiments in primate models, the DNA sequence encoding the PreM/M-Env protein was optimized using the genetic algorithm. This sequence was analyzed/optimized with respect to features such as "codon usage", secondary structure of messenger RNA (mRNA), distribution of GC content, repetitive DNA motives, restriction sites, "Splicing" critical sites, etc. The optimized sequence was sub cloned in 8L vector, generating p8L/YFEopt construction.

TABLE 2

Results of protection test in BALB/c and C57B1/6 mice comparing the 17DD vaccine with the DNA pL/YFE vaccine.

| Immunization/<br>Challenge<br>($10^5$ PFU/17DD<br>vaccine) | BALB/c<br>Mortality (Dead/<br>Inoculated) | C57B1/6<br>Mortality (Dead/<br>Inoculated) |
| --- | --- | --- |
| 17DD vaccine | 0/10 | 0/10 |
| pL/YFE | 0/10 | 0/10 |
| p43.2/empty or PBS | 8/10 | 10/10 |

TABLE 3

Comparison of the expression levels of the envelope proteins of Yellow Fever, wild and optimized, by flow cytometry.

| Plasmid | Expression normalized<br>by the Wild 2.<br>(%) |
| --- | --- |
| 1. p43.2/empty | 0.03 |
| 2. p43.2/ENV/c-LAMP/wild | 100 |
| 3. p43.2/ENV/c-LAMP/OPT-GA | 450 |
| 4. p43.2/ENV/c-LAMP/OPT-LT | 465 |
| 5. p8L/LAMP/empty | 0.00 |
| 6. p8L/ENV/c-LAMP/OPT-GA | 625 |
| 7. p8L/ENV/c-LAMP/OPT-LT | 350 |

The 17DD attenuated virus vaccine is the only formulation available to protect humans against infection caused by Yellow Fever Virus (YFV), major source of morbidity and mortality in tropical areas of the world. Despite the success of mass vaccination with the 17DD vaccine, which is capable of inducing durable response by neutralizing antibodies as cytotoxic response by T cells, adverse severe cases in consequence of the vaccination against Yellow Fever has been systematically reported in the literature. In some cases, the vaccination was directly associated with increasing severity of symptoms and may even lead to fatal reactions. In this scenario the development of new vaccination strategy, such as DNA vaccines encoding specific viral sequences, is of fundamental importance for the development of even safer vaccine strategies.

The DNA vaccine against Yellow Fever, according to the present invention, is based on the sequence encoding the envelope protein of YFV (p/YFE). In addition to wild con-

TABLE 1

| Oligonucleotides used to generate vaccine constructs p/YFE and pL/YFE | | |
| --- | --- | --- |
| Target Sequence | Primers used (forward X reverse) | |
| Wild PreM/M-E | 5'ACCG*CTCGAG*GCCACCATGGGAGGATTGTCCTCAAGGAAACG 3'<br>(SEQ ID NO: 1) (XhoI)<br>(Met)<br>5'ACCG*GCGGCCGC*TCAGTTCAAGCCGCCAAATAGCCCC 3'<br>(SEQ ID NO: 2) (NotI) (Stop) | |
| PreM/M-E for LAMP | 5'ACCG*GCTAGC*GCCACCATGGGAGGATTGTCCTCAAGGAAACG 3'<br>(SEQ ID NO: 3) (NheI) (Met)<br>5'ACCG*CTCGAG*GTTCAAGCCGCCAAATAGCCCC 3'<br>(SEQ ID NO: 4) (XhoI) | |
| LAMP (C-terminal) | 5'ACCG*CTCGAG*ACGCTGATCCCCATCGCTGTGG 3'<br>(SEQ ID NO: 5) (XhoI)<br>5'ACCG*TCTAGA*CTAGATAGTCTGGTAGCCTGCGTGACTCC 3'<br>(SEQ ID NO: 6) (XbaI) (Stop) | | struction p/YFE, the E sequence was also fused to the sequence encoding the human Lysosome-Associated Membrane Protein (h-LAMP), generating the construction (pL/YFE). The fusion with LAMP aims at directing the antigen to the antigen degradation/presentation MHCII pathway, as several works have demonstrated that the antigens fused to the LAMP (antigen/LAMP) are capable of generating a higher proliferative activity of specific antigen lymphocytes, high titers of antibodies and intense T-cytotoxic activity relative to wild non-fused antigens to the LAMP.

This invention aims at optimizing the DNA vaccine against YFV, p8L/YFEopt, to make it capable of protecting humans against infection caused by YFV. The development of this kind of technology aims at generating a vaccine even safer than the 17DD vaccine, which could revolutionize the vaccination strategy against YFV in Brazil and worldwide. Finally, the strategies used for the construction of this DNA vaccine mighty also serve as a subsidy for the development of other viral vaccines, especially against other flaviviruses such as Japanese encephalitis, West Nile Fever and Dengue virus.

REFERENCES CITED

1. Anwar, Chandrasekaran et al., 2005: Anwar et al., "West Nile premembrane-envelope genetic vaccine encoded as a chimera containing the transmembrane and cytoplasmic domains of a lysosome-associated membrane protein: increased cellular concentration of the transgene product, targeting to the MHC II compartment, and enhanced neutralizing antibody response", Virology 2005; 332(1): 66-77
2. Barrett, 2002: Barrett et al., "The epidemiology of yellow fever in Africa", Microbes and Infection 2002, 4(14): 1459-1468
3. Chen, Murphy et al., 1985: Chen et al., "Identification of two lysosomal membrane glycoproteins", J Cell Biol 1985, 101 (1): 85-95
4. De Arruda, Chikhlikar et al., 2004: De Arruda et al., "DNA vaccine encoding human immunodeficiency virus-1 Gag, targeted to the major histocompatibility complex II compartment by lysosomal-associated membrane protein, elicits enhanced long-term memory response", Immunology 2004; 112(1): 126-133
5. Donnelly, Berry et al., 2003: Donnelly et al., "Technical and regulatory hurdles for DNA vaccines", Int J Parasitol 2003, 33(5-6): 457-468
6. Donnelly, Ulmer et al. 1997: Donnelly et al., "DNA vaccines", Life Sci 1997, 60(3): 163-172
7. Drake, Lewis et al., 1999: Drake et al., "Involvement of MIIC-like late endosomes in B cell receptor-mediated antigen processing in murine B cells", J Immunol 1999; 162 (2): 1150-1155
8. Guarnieri, Arterburn et al., 1993: Guarnieri et al., "The motif Tyr-X-X-hydrophobic residue mediates lysosomal membrane targeting of lysosome-associated membrane protein 1", J Biol Chem 1993, 268(3): 1941-1946
9. Kleijmeer, Morkowski et al., 1997: Kleijmeer et al., "Major histocompatibility complex class II compartments in human and mouse B lymphoblasts represent conventional endocytic compartments", J Cell Biol 1997; 139(3): 639-649
10. Konishi, Yamaoka et al., 1998: Konishi et al., "Induction of protective immunity against Japanese encephalitis in mice by immunization with a plasmid encoding Japanese encephalitis virus premembrane and envelope genes", J Virol 1998; 72(6): 4925-4930
11. Konishi, Yamaoka et al., 2000: Konishi et al., "A DNA vaccine expressing dengue type 2 virus premembrane and envelope genes induces neutralizing antibody and memory B cells in mice", Vaccine 2000; 18(11-12): 1133-1139
12. Konishi, Ajiro. et al, 2003: Konishi et al., "Comparison of protective efficacies of plasmid DNAs encoding Japanese encephalitis virus proteins that induce neutralizing antibody or cytotoxic T lymphocytes in mice", Vaccine 2003, 21(25-26): 3675-3683
13. Lefeuvre, Marianneau et al., 2004: Lefeuvre et al., "Current Assessment of Yellow Fever and Yellow Fever Vaccine", Curr Infect Dis Rep 2004; 6(2): 96-104
14. Lewis and Babiuk, 1999: Lewis et al., "DNA vaccines: a review", Adv Virus Res 1999; 54: 129-188
15. Liu, 2003: Liu, M. A., "DNA vaccines: a review", J Intern Med 2003; 253(4): 402-410
16. Lu, et al Raviprakash, 2003: Lu et al., "Dengue 2 PreM-E/LAMP chimera targeted to the MHC class II compartment elicits long-lasting neutralizing antibodies", Vaccine 2003; 21(17-18): 2178-2189
17. Marques, Chikhlikar et al., 2003: Marques et al., "HIV-1 p55Gag encoded in the lysosome-associated membrane protein-1 as a DNA plasmid vaccine chimera is highly expressed, traffics to the major histocompatibility class II compartment, and elicits enhanced immune responses", J Biol Chem 2003; 278(39): 37926-37936
18. Monath, Arroyo et al., 2002: Monath et al., "Single mutation in the flavivirus envelope protein hinge region increases neurovirulence for mice and monkeys but decreases viscerotropism for monkeys: relevance to development and safety testing of live, attenuated vaccines", J Virol 2002; 76(4): 1932-1943
19. Obermüller, Kiecke et al., 2002: Obermüller et al., "The tyrosine motifs of Lamp 1 and LAP determine their direct and indirect targetting to lysosomes", J Cell Sci 2002; 115(Pt 1): 185-194
20. Poland, Calisher et al., 1981: Poland et al., "Persistence of neutralizing antibody 30-35 years after immunization with 17D yellow fever vaccine", Bull World Health Organ 1981; 59(6): 895-900
21. Raviprakash, Kochel et al., 2000: Raviprakash et al., "Immunogenicity of dengue virus type 1 DNA vaccines expressing truncated and full length envelope protein", Vaccine 2000; 18 (22): 2426-2434
22. Raviprakash, Marques et al., 2001: Raviprakash et al., "Synergistic neutralizing antibody response to a dengue virus type 2 DNA vaccine by incorporation of lysosome-associated membrane protein sequences and use of plasmid expressing GM-CSF", Virology 2001; 290(1): 74-82
23. Reinhardt, Jaspert et al., 1998: Reinhardt et al., "Development of viremia and humoral and cellular parameters of immune activation after vaccination with yellow fever virus strain 17D: a model of human flavivirus infection", J Med Virol 1998; 56(2): 159-167
24. Robinson, 1999: Robinson et al., "DNA vaccines: basic mechanism and immune responses (Review)", Int J Mol Med 1999; 4 (5): 549-555
25. Rohrer, Schweizer et al., 1996: Rohrer et al., "The targeting of Lamp1 to lysosomes is dependent on the spacing of its cytoplasmic tail tyrosine sorting motif relative to the membrane", J Cell Bio 1996; 132(4): 565-576
26. Rowell, Ruff et al., 1995: Rowell et al., "Lysosome-associated membrane protein-1-mediated targeting of the 26. HIV-envelope protein to an endosomal/lysosomal compartment enhances its presentation to MHC class II-restricted T cells", J Immunol 1995; 155(4): 1818-1828
27. Ruff, Guarneri et al., 1997: Ruff et al., "The enhanced immune response to the HIV gp160/LAMP chimeric gene product targeted to the lysosome membrane protein trafficking pathway", J Biol Chem 1997; 272(13): 8671-8678
28. Schultz, Pavlovic et al., 2000: Schultz et al., "Immune modulation in cancer using DNA inoculation—antitumour effect of interleukin-12", Dev Biol (Basel) 2000; 104: 109-114
29. Su, Vieweg et al., 2002: Su et al., "Enhanced induction of telomerase-specific CD4(+) T cells using dendritic cells transfected with RNA encoding a chimeric gene product", Cancer Res 2002; 62(17): 5041-5048
30. Turley, Inaba et al., 2000: Turley et al., "Transport of peptide-MHC class II complexes in developing dendritic cells", Science 2000; 288(5465): 522-527
31. Vasconcelos, Luna et al., 2001: Vasconcelos et al., "Brazilian Yellow Fever Vaccine Evaluation. Serious adverse events associated with yellow fever 17DD vaccine in Brazil: a report of two cases", Lancet 2001; 358(9276): 91-97
32. Wu, Li et al. 2006: Wu et al., "Development of an effective Japanese encephalitis virus-specific DNA vaccine", Microbes Infect 2006; 8(11): 2578-2586
33. Wu, Guarneri et al., 1995: Wu et al., "Engineering an intracellular pathway for major histocompatibility complex class II presentation of antigens", Proc Natl Acad Sci USA 1995; 92(25): 11671-11675

The invention claimed is:
1. An antigen comprising SEQ ID NO: 8 fused to a traffic signal LAMP.
2. An antigen comprising at least one genetic sequence fused to a traffic signal LAMP, wherein the at least one genetic sequence encodes at least one amino acid sequence encoded by SEQ ID NO: 8 or a homologous amino acid sequence with more than 80% homology thereto.
3. An antigen comprising at least one genetic sequence that encodes at least one yellow fever antigen of SEQ ID NO: 8, wherein the antigen is connected to a LAMP.
4. A DNA vaccine against Yellow Fever Virus comprising SEQ ID NO: 8 fused to a traffic signal LAMP.

* * * * *